(12) United States Patent
De Groot et al.

(10) Patent No.: US 8,126,677 B2
(45) Date of Patent: Feb. 28, 2012

(54) ANALYZING SURFACE STRUCTURE USING SCANNING INTERFEROMETRY

(75) Inventors: Peter De Groot, Middletown, CT (US); Xavier Colonna De Lega, Middlefield, CT (US)

(73) Assignee: Zygo Corporation, Middlefield, CT (US)

( * ) Notice: Subject to any disclaimer, the term of this patent is extended or adjusted under 35 U.S.C. 154(b) by 496 days.

(21) Appl. No.: 12/332,674

(22) Filed: Dec. 11, 2008

(65) Prior Publication Data

US 2009/0182528 A1    Jul. 16, 2009

Related U.S. Application Data

(60) Provisional application No. 61/013,732, filed on Dec. 14, 2007.

(51) Int. Cl.
*G01B 11/30* (2006.01)
*G01B 11/02* (2006.01)

(52) U.S. Cl. .................. 702/166; 356/512; 702/158

(58) Field of Classification Search ............. 702/74–76, 702/86, 151–155, 158, 159, 166, 167, 193; 356/489, 497, 511–514; 250/559.04
See application file for complete search history.

(56) References Cited

U.S. PATENT DOCUMENTS 2,612,074 A    9/1952   Mirau
(Continued)

FOREIGN PATENT DOCUMENTS

DE    4108944    9/1992
(Continued)

OTHER PUBLICATIONS

Abdulhalim, "Spectroscopic interference microscopy technique for measurement of layer parameters", Meas. Sci. Technol., vol. 12, pp. 1996-2001 (2001).

(Continued)

*Primary Examiner* — John H Le
(74) *Attorney, Agent, or Firm* — Fish & Richardson P.C.

(57) ABSTRACT

A method includes comparing a scanning interferometry signal obtained for a location of a test object to each of multiple model signals corresponding to different model parameters for modeling the test object, wherein for each model signal the comparing includes calculating a correlation function between the scanning interferometry signal and the model signal to identify a surface-height offset between the scanning interferometry signal and the model signal and, based on the identified surface-height offset, calculating a height-offset compensated merit value indicative of a similarity between the scanning interferometry signal and the model signal for a common surface height. The method further includes, based on the respective merit values for the different model signals, determining a test object parameter at the location of the test object.

33 Claims, 18 Drawing Sheets

U.S. PATENT DOCUMENTS

| | | |
|---|---|---|
| 4,188,122 A | 2/1980 | Massie et al. |
| 4,199,219 A | 4/1980 | Suzki et al. |
| 4,340,306 A | 7/1982 | Balasubramanian |
| 4,355,903 A | 10/1982 | Sandercock |
| 4,523,846 A | 6/1985 | Breckinridge et al. |
| 4,576,479 A | 3/1986 | Downs |
| 4,583,858 A | 4/1986 | Lebling et al. |
| 4,618,262 A | 10/1986 | Maydan et al. |
| 4,639,139 A | 1/1987 | Wyant et al. |
| 4,660,980 A | 4/1987 | Takabayashi et al. |
| 4,710,642 A | 12/1987 | McNeil |
| 4,806,018 A | 2/1989 | Falk |
| 4,818,110 A | 4/1989 | Davidson |
| 4,869,593 A | 9/1989 | Biegen |
| 4,923,301 A | 5/1990 | White |
| 4,948,253 A | 8/1990 | Biegen |
| 4,964,726 A | 10/1990 | Kleinknecht et al. |
| 4,999,014 A | 3/1991 | Gold et al. |
| 5,042,949 A | 8/1991 | Greenberg et al. |
| 5,042,951 A | 8/1991 | Gold et al. |
| 5,073,018 A | 12/1991 | Kind et al. |
| 5,112,129 A | 5/1992 | Davidson et al. |
| 5,129,724 A | 7/1992 | Brophy et al. |
| 5,133,601 A | 7/1992 | Cohen et al. |
| 5,135,307 A | 8/1992 | de Groot et al. |
| 5,153,669 A | 10/1992 | DeGroot |
| 5,164,790 A | 11/1992 | McNeil et al. |
| 5,166,751 A | 11/1992 | Massig |
| 5,173,746 A | 12/1992 | Brophy |
| 5,194,918 A | 3/1993 | Kino et al. |
| 5,241,369 A | 8/1993 | McNeil et al. |
| 5,301,010 A | 4/1994 | Jones et al. |
| 5,355,221 A | 10/1994 | Cohen et al. |
| 5,384,717 A | 1/1995 | Ebenstein |
| 5,386,119 A | 1/1995 | Ledger |
| 5,390,023 A | 2/1995 | Biegen |
| 5,398,113 A | 3/1995 | de Groot |
| 5,402,234 A | 3/1995 | Deck |
| 5,459,564 A | 10/1995 | Chivers |
| 5,471,303 A | 11/1995 | Ai et al. |
| 5,481,811 A | 1/1996 | Smith |
| 5,483,064 A | 1/1996 | Frey et al. |
| 5,539,517 A | 7/1996 | Cabib et al. |
| 5,543,841 A | 8/1996 | Kanamori |
| 5,555,471 A | 9/1996 | Xu et al. |
| 5,587,792 A | 12/1996 | Nishizawa et al. |
| 5,589,938 A | 12/1996 | Deck |
| 5,602,643 A | 2/1997 | Barrett |
| 5,633,714 A | 5/1997 | Nyyssonen |
| 5,640,270 A | 6/1997 | Aziz et al. |
| 5,703,692 A | 12/1997 | McNeil et al. |
| 5,757,502 A | 5/1998 | Weling |
| 5,774,224 A | 6/1998 | Kerstens |
| 5,777,740 A | 7/1998 | Lacey et al. |
| 5,777,742 A | 7/1998 | Marron |
| 5,784,164 A | 7/1998 | Deck et al. |
| 5,856,871 A | 1/1999 | Cabib et al. |
| 5,867,276 A | 2/1999 | McNeil et al. |
| 5,880,838 A | 3/1999 | Marx et al. |
| 5,900,633 A | 5/1999 | Solomon et al. |
| 5,912,741 A | 6/1999 | Carter et al. |
| 5,923,423 A | 7/1999 | Sawarti et al. |
| 5,943,134 A | 8/1999 | Yamaguchi et al. |
| 5,953,124 A | 9/1999 | Deck |
| 5,956,141 A | 9/1999 | Hayashi |
| 5,959,735 A | 9/1999 | Maris et al. |
| 5,963,329 A | 10/1999 | Conrad et al. |
| 6,028,670 A | 2/2000 | Deck |
| 6,160,621 A | 12/2000 | Perry et al. |
| 6,172,452 B1 | 1/2001 | Itaya et al. |
| 6,242,739 B1 | 6/2001 | Cherkassky |
| 6,249,351 B1 | 6/2001 | de Groot |
| 6,259,521 B1 | 7/2001 | Miller et al. |
| 6,275,297 B1 | 8/2001 | Zalicki |
| 6,377,349 B1 | 4/2002 | Fercher |
| 6,381,009 B1 | 4/2002 | McGahan |
| 6,392,749 B1 | 5/2002 | Meeks et al. |
| 6,417,109 B1 | 7/2002 | Jordan et al. |
| 6,429,943 B1 | 8/2002 | Opsal et al. |
| 6,449,048 B1 | 9/2002 | Olszak |
| 6,449,066 B1 | 9/2002 | Arns et al. |
| 6,483,580 B1 | 11/2002 | Xu et al. |
| 6,500,591 B1 | 12/2002 | Adams |
| 6,507,405 B1 | 1/2003 | Grek et al. |
| 6,525,825 B2 | 2/2003 | de Groot et al. |
| 6,545,761 B1 | 4/2003 | Aziz et al. |
| 6,545,763 B1 | 4/2003 | Kim et al. |
| 6,590,656 B2 | 7/2003 | Xu et al. |
| 6,597,460 B2 | 7/2003 | Groot et al. |
| 6,611,330 B2 | 8/2003 | Lee et al. |
| 6,624,894 B2 | 9/2003 | Olszak et al. |
| 6,633,389 B1 | 10/2003 | Poris et al. |
| 6,633,831 B2 | 10/2003 | Nikoonahad et al. |
| 6,636,322 B1 | 10/2003 | Terashita |
| 6,694,284 B1 | 2/2004 | Nikoonahad et al. |
| 6,714,307 B2 | 3/2004 | de Groot et al. |
| 6,721,094 B1 | 4/2004 | Sinclair et al. |
| 6,741,357 B2 | 5/2004 | Wang et al. |
| 6,741,360 B2 | 5/2004 | D'Agraives et al. |
| 6,775,006 B2 | 8/2004 | de Groot et al. |
| 6,775,009 B2 | 8/2004 | Hill |
| 6,822,745 B2 | 11/2004 | de Groot et al. |
| 6,856,384 B1 | 2/2005 | Rovira |
| 6,888,638 B1 | 5/2005 | Hill |
| 6,891,627 B1 | 5/2005 | Levy et al. |
| 6,909,509 B2 | 6/2005 | DeGroot |
| 6,925,860 B1 | 8/2005 | Poris et al. |
| 6,940,604 B2 | 9/2005 | Jung et al. |
| 6,956,658 B2 | 10/2005 | Meeks et al. |
| 6,956,660 B2 | 10/2005 | Meeks et al. |
| 6,985,232 B2 | 1/2006 | Sezginer |
| 6,989,905 B2 | 1/2006 | De Groot |
| 6,999,180 B1 | 2/2006 | Janik et al. |
| 7,012,700 B2 | 3/2006 | de Groot et al. |
| 7,018,271 B2 | 3/2006 | Wiswesser et al. |
| 7,038,850 B2 | 5/2006 | Chang et al. |
| 7,046,371 B2 | 5/2006 | de Lega et al. |
| 7,061,623 B2 | 6/2006 | Davidson |
| 7,068,376 B2 | 6/2006 | De Groot |
| 7,088,451 B2 | 8/2006 | Sezginer |
| 7,102,761 B2 | 9/2006 | de Lega et al. |
| 7,106,454 B2 | 9/2006 | De Groot et al. |
| 7,119,909 B2 | 10/2006 | Unruh et al. |
| 7,139,081 B2 | 11/2006 | De Groot |
| 7,139,083 B2 | 11/2006 | Fielden et al. |
| 7,142,311 B2 | 11/2006 | De Lega |
| 7,177,030 B2 | 2/2007 | Leizerson |
| 7,205,518 B2 | 4/2007 | Neuvonen |
| 7,239,398 B2 | 7/2007 | de Groot et al. |
| 7,271,918 B2 | 9/2007 | de Groot et al. |
| 7,283,248 B2 | 10/2007 | Hill |
| 7,289,225 B2 | 10/2007 | de Groot |
| 7,298,494 B2 | 11/2007 | de Groot |
| 7,304,747 B2 | 12/2007 | de Lega |
| 7,315,382 B2 | 1/2008 | de Groot |
| 7,324,210 B2 | 1/2008 | de Groot et al. |
| 7,324,214 B2 | 1/2008 | de Groot et al. |
| 7,428,057 B2 | 9/2008 | De Lega et al. |
| 2002/0015146 A1 | 2/2002 | Meeks et al. |
| 2002/0135775 A1 | 9/2002 | de Groot et al. |
| 2002/0148955 A1 | 10/2002 | Hill |
| 2002/0196450 A1 | 12/2002 | Olszak et al. |
| 2003/0011784 A1 | 1/2003 | de Groot et al. |
| 2003/0048458 A1 | 3/2003 | Mieher et al. |
| 2003/0075721 A1 | 4/2003 | Li |
| 2003/0112444 A1 | 6/2003 | Yang et al. |
| 2003/0137671 A1 | 7/2003 | de Groot et al. |
| 2003/0197871 A1 | 10/2003 | de Groot |
| 2004/0027576 A1 | 2/2004 | de Groot et al. |
| 2004/0075843 A1 | 4/2004 | Marron et al. |
| 2004/0085544 A1 | 5/2004 | de Groot |
| 2004/0185582 A1 | 9/2004 | Kueny |
| 2004/0189999 A1 | 9/2004 | de Groot et al. |
| 2004/0233442 A1 | 11/2004 | Mieher et al. |
| 2004/0233444 A1 | 11/2004 | Mieher et al. |
| 2004/0246493 A1 | 12/2004 | Kim et al. |
| 2005/0024773 A1 | 2/2005 | Lille |

| | | | |
|---|---|---|---|
| 2005/0057757 A1 | 3/2005 | de Lega et al. | |
| 2005/0068540 A1 | 3/2005 | de Groot et al. | |
| 2005/0073692 A1 | 4/2005 | de Groot et al. | |
| 2005/0078318 A1 | 4/2005 | de Groot | |
| 2005/0078319 A1 | 4/2005 | de Groot | |
| 2005/0088663 A1 | 4/2005 | de Groot et al. | |
| 2005/0146727 A1 | 7/2005 | Hill | |
| 2005/0179911 A1 | 8/2005 | Boomgarden et al. | |
| 2005/0225769 A1 | 10/2005 | Bankhead et al. | |
| 2005/0237534 A1 | 10/2005 | Deck | |
| 2005/0237537 A1 | 10/2005 | Leizerson et al. | |
| 2006/0012582 A1 | 1/2006 | de Lega | |
| 2006/0072104 A1 | 4/2006 | Engel et al. | |
| 2006/0119841 A1 | 6/2006 | Saunders et al. | |
| 2006/0158657 A1 | 7/2006 | de Lega et al. | |
| 2006/0158658 A1 | 7/2006 | de Lega et al. | |
| 2006/0158659 A1 | 7/2006 | de Lega et al. | |
| 2006/0170932 A1 | 8/2006 | Hayashi et al. | |
| 2006/0187465 A1 | 8/2006 | de Groot | |
| 2006/0262321 A1 | 11/2006 | de Groot | |
| 2007/0008551 A1 | 1/2007 | Tang | |
| 2007/0046953 A1* | 3/2007 | De Groot et al. | 356/512 |
| 2007/0081167 A1 | 4/2007 | de Groot | |
| 2007/0086013 A1 | 4/2007 | de Lega et al. | |
| 2007/0091317 A1 | 4/2007 | Freischlad et al. | |
| 2007/0091318 A1 | 4/2007 | Freischlad et al. | |
| 2007/0091940 A1 | 4/2007 | Jameson | |
| 2007/0097380 A1 | 5/2007 | de Groot et al. | |
| 2007/0127036 A1 | 6/2007 | Liao et al. | |
| 2007/0139656 A1 | 6/2007 | Wan | |
| 2007/0247637 A1 | 10/2007 | de Groot et al. | |
| 2008/0018901 A1 | 1/2008 | de Groot | |
| 2008/0088849 A1 | 4/2008 | de Lega et al. | |
| 2008/0174784 A1 | 7/2008 | de Lega et al. | |

FOREIGN PATENT DOCUMENTS

| | | |
|---|---|---|
| DE | 4309056 | 9/1994 |
| EP | 0 397 388 | 11/1990 |
| EP | 0 549 166 | 6/1993 |
| EP | 0 617 255 | 9/1994 |
| EP | 0 929 094 | 7/1999 |
| GB | 2385417 | 8/2003 |
| JP | 8327327 | 12/1996 |
| JP | 09-218016 | 8/1997 |
| JP | 2000121317 | 4/2000 |
| JP | 2000-180124 | 6/2000 |
| JP | 2001-141652 | 5/2001 |
| JP | 2001-272603 | 10/2001 |
| WO | WO 93/24805 | 12/1993 |
| WO | WO 94/00733 | 1/1994 |
| WO | WO 95/09343 | 4/1995 |
| WO | WO 97/44633 | 11/1997 |
| WO | WO 02/082008 | 10/2002 |
| WO | WO 03/062802 | 7/2003 |
| WO | WO 2004/023071 | 3/2004 |
| WO | WO 2005/029192 | 3/2005 |

OTHER PUBLICATIONS

Akcay, C. et al., "Spectral shaping to improve the point spread function in optical coherence tomography", Optics Letters, vol. 28, No. 20, pp. 1921-1923 (Oct. 15, 2003).

Azzam, R.M.A. et al, "Ellipsometric function of a film-substrate system: Applications to the design of reflection-type optical devices and to ellipsometry", Journal of the Optical Society of America, vol. 5, No. 3, pp. 252-260 (1975).

Azzam, R.M.A. et al., "Reflection and Transmission of Polarized Light by Stratified Planar Structures", Ellipsometry and Polarized Light, Elsevier Science B.V. ISBN 0 444 87016 4 (Paperback) pp. 267-363 (1987).

Bashkansky, M. et al., "Signal Processing for Improving Field Cross-correlation Function in Optical Coherence Tomography", Supplement to Optics & Photonics News, 9(5) (May 1998).

Biegen, "Determination of the Phase Change on Reflection from Two-beam Interference," Optics Letters, 19:21:1690-1692, Nov. 1, 1994.

Bosseboeuf, A. et al., "Application of microscopic interferometry techniques in the MEMS field", Proc. SPIE, 5145, pp. 1-16 (2003).

Chim, S. S. C. and Kino, G. S., "Three-Dimensional Image Realization in Interference Microscopy", Applied Optics, May 10, 1992, vol. 31, No. 14.

Creath, Katherine, "Step height measurement using two-wavelength phase-shifting interferometry", Applied Optics, vol. 26, No. 14, pp. 2810-2816 (Jul. 15, 1987).

Danielson et al., "Absolute Optical Ranging Using Low Coherence Interferometry," Applied Optics, 30:21:2975-2979, Jul. 20, 1991.

Davidson, M. et al., "An Application of Interference Microscopy to Integrated Circuit Inspection and Metrology", Proceedings of SPIE, vol. 775, pp. 233-247 (1987).

de Groot et al., "Angle-resolved three-dimensional analysis of surface films by coherence scanning interferometry", Optics Letters, vol. 32, No. 12, pp. 1638-1640 (Jun. 15, 2007).

de Groot et al.; "Three-dimensional imaging by sub-Nyquist sampling of white-light interfergrams"; Optics Letters vol. 18, No. 17; pp. 1462-1464, Sep. 1, 1993.

de Groot, P. et al., "Determination of fringe order in white-light interference microscopy", Appl. Opt., 41(22) pp. 4571-4578 (2002).

de Groot, P. et al., "Signal modeling for low coherence height-scanning interference microscopy", Applied Optics, vol. 43 No. 25, pp. 4821-4830 (Sep. 1, 2004).

de Groot, P. et al., "Signal modeling for modern interference microscopes", SPIE Proceedings vol. 5457, pp. 26-34 (2004).

de Groot, P., "Extending the unambiguous range of two-color interferometers", Applied Optics, vol. 33, No. 25, pp. 5948-5953 (Sep. 1, 1994).

de Groot, P., "Derivation of algorithms for phase-shifting interferometry using the concept of a data-sampling window", Appl. Opt., 34(22), p. 4723-4730 (1995).

de Groot, P., "Phase-shift calibration errors in interometers with spherical Fizeua cavities," Applied Optics, vol. 34:16, pp. 2856-2863 (Jun. 1, 1995).

de Groot, P., "Three-color laser-diode interferometer", Applied Optics, vol. 30, No. 25, pp. 3612-3616 (Sep. 1, 1991).

de Lega, X., et al., "Optical topography measurement of patterned wafers," American Institute of Physics Conference Proceedings, vol. 788, pp. 432-436 (2005).

Deck, L. et al., "Two-color light-emitting-diode source for high-precision phase-shifting interferometry", Optics Letters, vol. 18, No. 22, pp. 1899-1901 (Nov. 15, 1993).

Dresel et al., "Three Dimensional Sensing of Rough Surfaces by Coherence Radar, " Applied Optics, 31:7:919-925, Mar. 1, 1992.

Feke, Gilbert D. et al., "Interferometric back focal plane microellipsometry", Applied Optics, vol. 37, No. 10, pp. 1796-1802 (Apr. 1, 1998).

Flournoy, P.A. et al., "White-light interferometric thickness gauge", Appl. Opt., 11(9), pp. 1907-1915 (1972).

Gale, D.M. et al., "Linnik microscope imaging of integrated circuit structures", Applied Optics vol. 35, No. 1, pp. 131-148 (Jan. 1, 1996).

Ghiglia, Dennis C. et al., "Quality-Guided Path Following", Two-Dimensional Phase Unwrapping—Theory, Algorithms and Software, John Wiley & Sons publishers, ISBN 0-471-24935-1, pp. 122-136 (1998).

Hausler, G. et al., "Coherence Radar and Spectral Radar—New Tools for Dermatological Diagnosis", Journal of Biomedical Optics, vol. 3, No. 1, pp. 21-31 (Jan. 1998).

Hecht, "Basics of Coherence Theory," Optics, 2nd Ed., Addison Wesley, pp. 516-517 (1987).

Holmes, R.D. et al., "Scanning microellipsometry for extraction of true topography", Electronics Letters, vol. 31, No. 5, pp. 358-359 (Mar. 2, 1995).

J.E. Greivenkamp, "Generalized data reduction for heterodyne interferometry", Opt. Eng., vol. 23 No. 4, pp. 350-352 (Jul./Aug. 1984).

Kim, Seung-Woo et al., "Thickness-profile measurement of transparent thin-film layers by white-light scanning interferometry", Applied Optics, vol. 38, No. 28, pp. 5968-5973 (Oct. 1, 1999).

Kino et al., "Mirau Correlation Microscope," Applied Optics, 29:26:3775-3783, Sep. 10, 1990.

Kohlhaas, A. Fromchen, C. and Brinkmeyer, E., "High-Resolution OCDR for Testing Integrated-Optical Waveguides: Dispersion-Corrupted Experimental Data Corrected by a Numerical Algorithm", Journal of Lightwave Technology, Nov. 1991, vol. 9, No. 11.

Kujawinska, Malgorzata, "Spatial Phase Measurement Methods", Interferogram Analysis: Digital Fringe Pattern Measurement Techniques, IOP Publishing Ltd. 1993, pp. 141-193.

Larkin, Kieran G., "Efficient nonlinear algorithm for envelope detection in white light interferometry", J. Opt. Soc. Am A4, pp. 832-843 (1996).

Lee et al., "Profilometry with a coherence scanning microscope", Appl. Opt., 29(26), pp. 3784-3788 (1990).

Lee-Bennett, I., "Advances in non-contacting surface metrology", OF&T Workshop, paper OTuC1 (2004).

Leonhardt, K. et al., "Micro-Ellipso-Height-Profilometry", Optics Communications, vol. 80, No. 3, 4, pp. 205-209 (Jan. 1, 1991).

Liu, Y. et al., "Common path interferometric microellipsometry", SPIE, vol. 2782, pp. 635-645 (1996).

Lyakin et al., "The interferometric system with resolution better than coherence length for determination of geometrical thickness and refractive index of a layer object", Proceedings of the SPIE—The International Society for Optical Engineering SPIE-INT, Soc. Opt. Eng USA, vol. 4956, pp. 163-169 (Jul. 2003).

Morgan, C.J., "Least-Squares estimation in phase-measurement interferometry", Apt. Let., 7(8), pp. 368-370 (1982).

Ngoi et al., "Phase-shifting interferometry immune to vibration", Applied Optics, vol. 40, No. 19, pp. 3211-3214 (2001).

Novak et al., "Template-based software for accurate MEMS characterization", Proceedings of SPIE, Fol. 4980, pp. 75-80 (2003).

Onodera, Ribun et al., "Two-wavelength interferometry that uses a Fourier-transform method", Applied Optics, vol. 37, No. 34, pp. 7988-7994 (Dec. 1, 1998).

Oppenheim, A.V. et al., "10.3: The time-dependent Fourier Transform", Discrete-Time Signal Processing, 2.sup.nd Edition, pp. 714-722 (Prentice Hall, New Jersey, 1999).

Park et al., "Direct Quadratic Polynomial Fitting for Fringe Peak Detection of White Light Scanning Interferograms," Opt. Eng., 39:4:952-959, Apr. 2000.

Pelligrand, S. et al., "Mesures 3D de topographies et de vibrations a l'echelle (sub)micrometrique par microscopie optique interferometrique", Proc. Club CMOI, Methodes et Techniques Optiques pour l'Industrie (2002).

Pfortner, Andreas et al., "Red-green-blue interferometer for the metrology of discontinuous structures", Applied Optics, vol. 42, No. 4, pp. 667-673 (Feb. 1, 2003).

Pluta, Maksymilian, "Advanced Light Microscopy", vol. 3, (Elsevier, Amsterdam, 1993) pp. 265-271.

Press, W.H. et al., "Linear Correlation", Numerical Recipes in C, Cambridge University Press, 2.sup.nd Edition, pp. 636-639 (1992).

Rosencwaig, Allan et al., "Beam profile reflectometry: A new technique for dielectric film measurements", Applied Physics Letters, vol. 60, No. 11, pp. 1301-1303 (Mar. 16, 1992).

Sandoz, P. et al., "High-resolution profilometry by using phase calculation algorithms for spectroscopic analysis of white-light interferograms", Journal of Modern Optics, vol. 43, No. 4, pp. 701-708 (1996).

Sandoz, P. et al., "Optical implementation of frequency domain analysis for white light interferometry", Proceedings SPIE, vol. 2545, pp. 221-228 (Jun. 1995).

Sandoz, P. et al., "Processing of white light correlograms: simultaneous pahse and envelope measurements by wavelet transformation", SPIE, 3098, pp. 73-82 (1997).

Sandoz, Patrick "Wavelet transform as a processing tool in white-light interferometry", Optics Letters, vol. 22, No. 14, pp. 1065-1067 (Jul. 15, 1997).

Schmit, J. et al., "Extended averaging technique for derivation of error-compensating algorithms in phase-shifting interferometry," Applied Optics, vol. 34:19, pp. 3610-3619 (Jul. 1, 1995).

Schnell, U. et al., "Dispersive white-light interferometry for absolute distance measurement with dielectric multilayer systems on the target", Optics Letters, vol. 21, No. 7, pp. 528-530 (Apr. 1996).

Schwider, J. et al., "Dispersive interferometric profilometer", Optics Letters, vol. 19, No. 13, pp. 995-997 (Jul. 1994).

See et al, Scanning optical microellipsometer for pure surface profiling, Applied Optics, Dec. 1996, pp. 6663-6668.

See, C.W. et al., "Scanning optical microellipsometer for pure surface profiling", Applied Optics, vol. 35, No. 34, pp. 6663-6668 (Dec. 1, 1996).

Shatalin, S. V. et al., "Reflection conoscopy and micro-ellipsometry of isotropic thin film structures", Journal of Microscopy, vol. 179, Part 3, pp. 241-252 (Sep. 1995).

Sheppard et al., "Effect of numerical aperture on interference fringe spacing", Applied Optics, vol. 34, No. 22, pp. 4731-4734 (Aug. 1, 1995).

Totzeck, M., "Numerical simulation of high-NA quantitative polarization microscopy and corresponding near-fields", Optik, vol. 112, No. 9, pp. 399-406 (2001).

Tripathi, R. et al., "Spectral shaping for non-Gaussian source spectra in optical coherence tomography", Optics Letters, vol. 27, No. 6, pp. 406-408 (2002).

Tzannes, A.P. et al., "Measurement of the modulation transfer function of infrared cameras," Optical Engineering, vol. 34, No. 6, pp. 1808-1817 (Jun. 1995).

Willenborg, D. et al, "A novel micro-spot dielectric film thickness measurement system", SPIE, vol. 1594, pp. 322-333 (1991).

Wyant, "Phase shifting interferometry" (1998).

Youngquist, R. C. Carr, S. and Davies, D. E. N., "Optical Coherence-Domain Reflectometry: a New Optical Evaluation Technique", Optical Letters, Mar. 1987, vol. 12, No. 3.

Berman et al., "Review of In Situ & In-line Detection for CMP Applications," Semiconductor Fabtech—8th Edition, pp. 267-274 (1998).

* cited by examiner

+ + Experimental signal
—— Model signal

ANALYZING SURFACE STRUCTURE USING SCANNING INTERFEROMETRY

CROSS-REFERENCE TO RELATED APPLICATIONS

This application claims priority to Provisional Application No. 61/013,732, entitled "ANALYZING SURFACE STRUCTURE USING SCANNING INTERFEROMETRY," filed on Dec. 14, 2007, the entire contents of which is incorporated herein by reference.

TECHNICAL FIELD

The disclosure relates to using scanning interferometry to analyze the surface structure of a test object, and more particularly, to analyze the surface topography and/or features of a complex surface structure of the test object.

BACKGROUND

Scanning interferometry is used to gain information about a test object. Information about, for example, the surface structure can be relevant to flat-panel display (FPD) metrology, e.g., the characterization of FPD components, semiconductor wafer metrology, and in-situ analysis of thin films and dissimilar materials. Examples of relevant information include besides the surface topography itself, features of a complex surface structure, such as thin film parameters (thickness or index of refraction), discrete structures of dissimilar materials, and discrete structures that are under-resolved by the optical resolution of an interference microscope.

Interferometric techniques are commonly used to measure the profile of a surface of an object. To do so, an interferometer combines measurement light reflected from the surface of interest with reference light reflected from a reference surface to produce an interferogram. Fringes in the interferogram are indicative of spatial and structural variations between the surface of interest and the reference surface.

A scanning interferometer scans the optical path length difference (OPD) between the reference and measurement light of the interferometer over a range comparable to or larger than the coherence length of the interfering light. For multiple scan-positions, a detector measures the intensity of the interfering light, which is the basis for a scanning interferometry signal (hereafter also interferometry signal). For surface interferometry, for example, multiple camera pixels can be used to measure a spatial interferogram at each scan position, with each camera pixel measuring an interferometry signal for a corresponding location of the test surface over the range of scan positions. An interferometry signal is typically characterized by a sinusoidal carrier modulation (the "fringes") with bell-shaped fringe-contrast envelope.

A limited coherence length of the interfering light can be produced, for example, by using a white-light source, which is referred to as scanning white light interferometry (SWLI). A typical SWLI signal features a few fringes localized near the zero OPD position which is defined as an equal optical path length for the reference and measurement light.

The conventional idea underlying interferometric metrology is to derive features of an object from the interferometry signal. The analysis can be performed in a scan domain, i.e., using the interferometry signal depending on the scan-coordinate, or in a frequency domain, i.e., using an interferometry spectrum derived from the interferometry signal.

For surface profiling, the first approach includes, for example, to locate the peak or center of the envelope, assuming that this position corresponds to the zero OPD of a two-beam interferometer for which one beam reflects from the object surface. The second approach includes, for example, calculating the rate of change of the phase of the transformed interferometry signal with the wavelength, assuming that an essentially linear slope is directly proportional to a surface height of the test object. This latter approach is referred to as Frequency Domain Analysis (FDA). See, for example, U.S. Pat. No. 5,398,113, U.S. Pat. No. 7,106,454, U.S. Pat. No. 7,271,918, the contents of which are herein incorporated by reference.

Conventional techniques used for surface characterization (e.g., ellipsometry and reflectometry) rely on the fact that the complex reflectivity of an unknown optical interface depends both on its intrinsic characteristics (material properties and thickness of individual layers) and on three properties of the light that is used for measuring the reflectivity: wavelength, angle of incidence, and polarization state. In practice, characterization instruments record reflectivity fluctuations resulting from varying these parameters over known ranges.

SUMMARY

Scanning interferometers can be used to analyze surface structure of a test object based on an interferometry signal. The analysis of the interferometry signal can involve a comparison of the interferometry signal with a set of model signals, each model signal being indicative for a specific feature (parameter) of the object, for which it is modeled. The comparison yields a merit value on that the determination of a test object parameter is based.

In general, in a first aspect, the invention features a method that includes comparing a scanning interferometry signal obtained for a location of a test object to each of multiple model signals corresponding to different model parameters for modeling the test object, wherein for each model signal the comparing comprises calculating a correlation function between the scanning interferometry signal and the model signal to identify a surface-height offset between the scanning interferometry signal and the model signal and, based on the identified surface-height offset, calculating a height-offset compensated merit value indicative of a similarity between the scanning interferometry signal and the model signal for a common surface height. The method further includes, based on the respective merit values for the different model signals, determining a test object parameter at the location of the test object.

In another aspect, an interferometer includes an optical system configured to obtain an scanning interferometry signal from a surface location of an object and a processor. The processor includes code configured to:

i) receive multiple model signals corresponding to different model parameters for modeling the test object, compare the scanning interferometry signal to each of multiple model signals, wherein for each model signal the comparing comprises calculating a correlation function between the scanning interferometry signal and the model signal to identify a surface-height offset between the scanning interferometry signal and the model signal and, based on the identified surface-height offset, calculating a height-offset compensated merit value indicative of a similarity between the scanning interferometry signal and the model signal for an approximated common surface height; and ii) based on the respective merit values for the different model signals, determine a test object parameter at the location of the test object.

In another aspect, a method includes comparing a scanning interferometry signal obtained for each of multiple locations of a test object to each of multiple model signals corresponding to different model parameters for modeling the test object, wherein for each test object location and each model signal the comparing comprises calculating a correlation function between the scanning interferometry signal and the model signal based on a frequency domain representation of the scanning interferometry signal and a frequency domain representation of the model signal to identify a surface-height offset between the scanning interferometry signal and the model signal and, based on the identified surface-height offset, calculating a height-offset compensated merit value indicative of a similarity between the scanning interferometry signal and the model signal for a common surface height. The method further includes, based on the respective merit values for the different model signals at each of the different test object locations, determining one or more test object parameters at each test object location.

In another aspect, a method includes, for at least one model signal of a set of model signals, calculating a height-offset compensated merit value indicative of a similarity between a scanning interferometry signal and the model signal for a common surface height, wherein calculating the height-offset compensated merit value includes performing a correlation of the scanning interferometry signal or information derived thereof and the model signal or information derived thereof, and based on the correlation, determining a height-dependent phase slope between a frequency domain representation of the interferometry signal and a frequency domain representations of the model signal and compensating the phases of the coefficients of at least one of the frequency domain representations of the interferometry signal and the model signal. The method further includes, based on the height-offset compensated merit value, determining a test object parameter.

Implementations may include one or more of the following features.

In some embodiments, the calculated correlation function can be based on a frequency domain representation of the scanning interferometry signal and a frequency domain representation of the model signal.

In some embodiments, calculating the correlation function can include inverse transforming the product of the frequency domain representations of the scanning interferometry signal and the model signal into the scan coordinate domain.

In some embodiments, the identified surface-height offset can correspond to a peak in the calculated correlation function. The peak can be determined by interpolating the correlation function between scan-positions.

In some embodiments, identifying the surface-height offset can include determining a phase difference between the scanning interferometry signal and the model signal.

In some embodiments, determining the phase difference can include determining a complex phase of the correlation function at a peak positioning the correlation function.

In some embodiments, calculating the height-offset compensated merit value can include compensating a frequency domain representation of the scanning interferometry signal or a frequency domain representation of the model signal with a linear phase term having a slope corresponding to the identified surface-height offset and quantifying the similarity between the scanning interferometry signal and the model signal following the phase compensation.

The quantification of the similarity between the scanning interferometry signal and the model signal following the phase compensation can be performed in the frequency domain.

In some embodiments, a phase compensation can be applied to the frequency domain representation of the scanning interferometry signal to produce a frequency domain representation of the scanning interferometry signal corresponding to a surface height common to that used for modeling the model signal.

The phase compensation of the frequency domain representation of the interferometry signal can include multiplying a spectral component with a linear phase factor $\exp(-iK\zeta_{offset})$, where K is the fringe frequency component and $\zeta_{offset}$ is the identified surface-height offset.

The phase compensation of the frequency domain representation of the interferometry signal can include multiplying a spectral component with a phase factor $\exp(-iA_{peak})$, where $A_{peak}$ is the complex phase of the correlation function at a peak of the calculated correlation function.

The phase compensation of the frequency domain representation of the interferometry signal can include removing a linear portion of the phase change within the spectrum.

The phase compensation comprises removing a phase difference between the interferometry spectrum and the model spectrum arising from the surface-height offset between the scanning interferometry signal and the model signal.

In some embodiments, calculating the height-offset compensated merit value can be based on a frequency domain representation of the scanning interferometry signal and a frequency domain representation of the model signal.

In some embodiments, calculating the height-offset compensated merit value can be restricted to a region of interest in the frequency domain.

In some embodiments, calculating the height-offset compensated merit value can be based on a least-square difference between the phase-compensated interferometry spectrum and the model spectrum.

In some embodiments, calculating the height-offset compensated merit value can be based on a complex phase of the correlation function at the peak position.

In some embodiments, calculating the height-offset compensated merit value can be based on the peak value of the correlation function at the peak position.

In some embodiments, calculating the height-offset compensated merit value can be based on normalizing the frequency domain representation of the scanning interferometry signal or the frequency domain representation of the model signal.

In some embodiments, the model parameters corresponding to the model signal can include one or more of thin film thickness and thin film index. The model parameters corresponding to the model signals can further include one or more parameters relating to an under-resolved surface feature.

In some embodiments, the under-resolved surface feature can be an array feature defining a diffractive grating.

In some embodiments, determining a test object parameter can include determining more than one test object parameter based on the respective merit values.

In some embodiments, the determined test object parameter can correspond to one or more of surface height, thin film thickness, and thin film index of refraction. The determined test object parameter can further correspond to one of the model parameters for the model signals.

In some embodiments, determining a test object parameter can include identifying a matching model signal based on comparing the height-offset compensated merit values.

Determining the test object parameter can be based on the matching model signal.

In some embodiments, determining the test object parameter can include corrections based on a complex phase of the correlation function at the peak.

In some embodiments, the method can further include outputting the test object parameter.

In some embodiments, comparing a scanning interferometry signal to each of multiple model signals and determining a test object parameter can be repeated for each of multiple scanning interferometry signals corresponding to different surface locations of the test object.

In some embodiments, the method can further include obtaining the scanning interferometry signals for the multiple surface locations.

In some embodiments, the scanning interferometry signals for the multiple surface locations can be obtained using a scanning interferometer that images the multiple locations onto an imaging detector.

In some embodiments, the interferometry signal can be obtained by imaging test light emerging from the test object to interfere with reference light on a detector, and varying an optical path length difference from a common source to the detector between interfering portions of the test and reference light, wherein the test and reference light are derived from the common source, and wherein the interferometry signal corresponds to an interference intensity measured by the detector as the optical path length difference is varied.

In some embodiments, the test and reference light can have a spectral bandwidth greater than 5% of a central frequency for the test and reference light.

The common source can have a spectral coherence length, and the optical path length difference can be varied over a range larger than the spectral coherence length to produce the scanning interferometry signal.

In some embodiments, optics used to direct test light onto the test object and image it to the detector can define a numerical aperture for the test light greater than 0.8.

In some embodiments, the method can further include accounting for systematic contributions to the scanning interferometry signal arising from a scanning interferometer system used to acquire the scanning interferometry signal. The method can further include calibrating the systematic contributions of the scanning interferometry system using a test-object having known properties.

In some embodiments of the interferometer, the code can be further configured to transform the scanning interferometer signal and the model signal into the frequency domain and calculate the correlation function based in the transformed signals.

In some embodiments, the code can be further configured to compensate a frequency domain representation of the scanning interferometry signal or a frequency domain representation of the model signal with a linear phase term having a slope corresponding to the identified surface-height offset and quantifying the similarity between the scanning interferometry signal and the model signal following the phase compensation.

In some embodiments, the processor can further include code configured to generate one of the model signals based on model parameters.

In some embodiments, the code can be also configured to determine a test object parameter map associated with a surface of the test object. The test object parameter map can be based on a height parameter, on a thin film parameter, and/or on an under-resolved surface feature parameter.

In some embodiments, the processor can be further configured to output information about the determined test object parameter.

In some embodiments, the optical system can include a multi-element detector configured to obtain an interferometry signal from each of multiple surface locations of the object, and wherein the processor is configured to determine information about a test object parameter at each of the multiple surface locations based on the obtained interferometry signals.

In another aspect, the invention features a process for making a display panel, including providing a component of the display panel, determining information about the component using a method or interferometer discussed with respect to the aforementioned aspects, wherein the component corresponds to the test object and the information is based on the test object parameter, and forming the display panel using the component.

Implementations of the process can include one or more of the following features and/or features of other aspects. For example, the component can include a pair of substrates separated by a gap and the information comprises information about the gap. Forming the display panel can include adjusting the gap based on the information. In some embodiments, forming the display panel includes filling the gap with a liquid crystal material.

The component can include a substrate and a layer of a resist on the substrate. The information can include information about the thickness of the layer of resist. The layer of resist can be a patterned layer, and the information can include information about a dimension or an overlay error of a feature of the patterned layer. Forming the display can include etching a layer of material under the layer of resist.

The component can include a substrate that includes spacers and the information can include information about the spacers. Forming the display can include modifying the spacers based on the information.

The details of one or more embodiments are set forth in the accompanying drawings and the description below. Other features and advantages will be apparent from the description and drawings, and from the claims.

BRIEF DESCRIPTION OF THE DRAWINGS

Like reference numerals in different drawings refer to common elements.

DETAILED DESCRIPTION

Scanning interferometers can be used to analyze surface structure of an object by comparing interferometry signals with model signals. Examples of surface structure include surface heights, material composition, film thickness, and optically-under-resolved surface structure. Applications for scanning interferometry include semiconductor wafer inspection, flat panel display process control, and general laboratory use. A specific example is the measurement of the photoresist thickness in the halftone region of thin film transistors used for flat panel displays.

Figure 1:
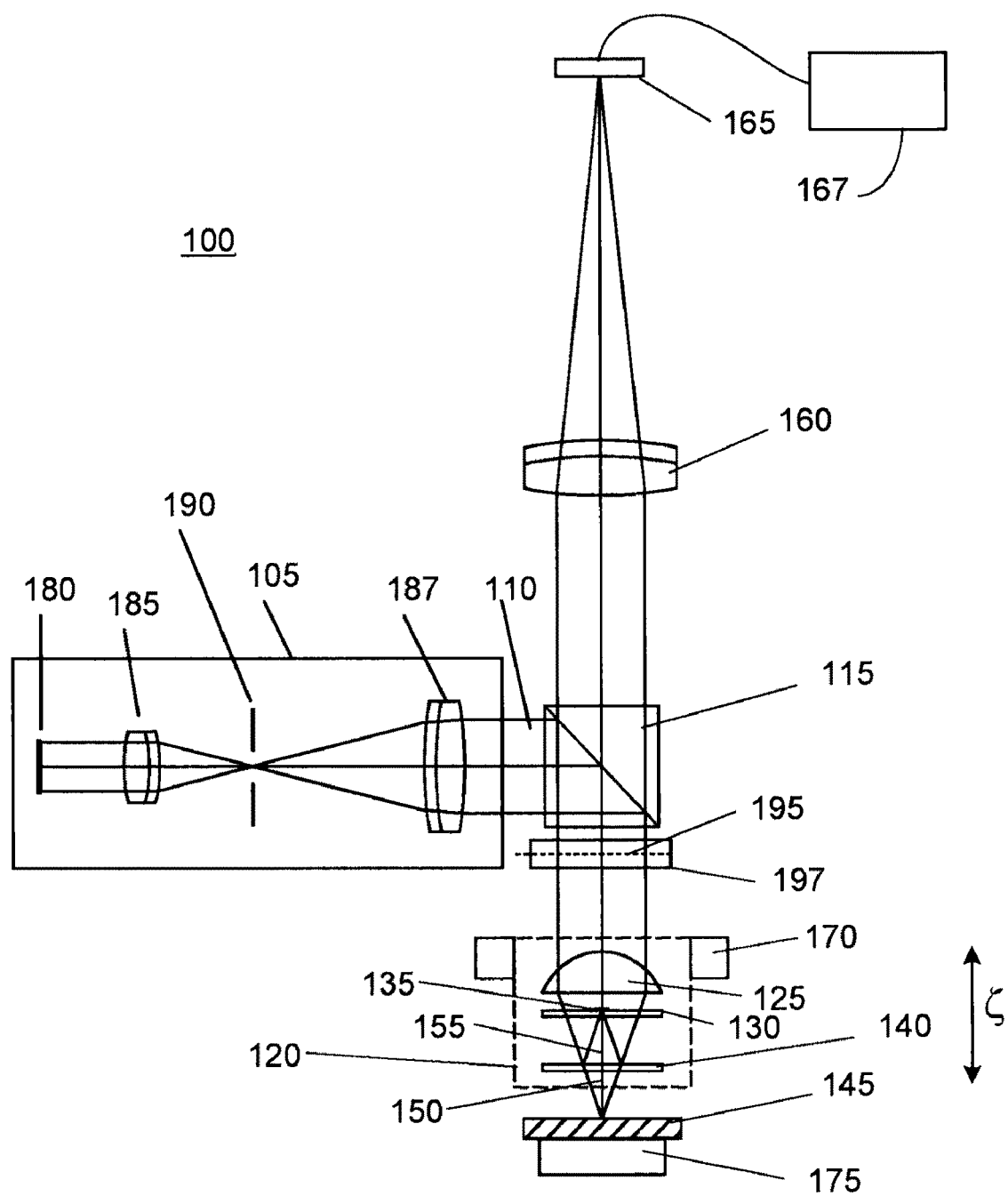
FIG. 1 is a schematic drawing of a Mirau-type scanning interferometry system.

The measured interference signal is acquired with an interferometry system, such as interferometry system 100 shown in FIG. 1. The interferometry system 100 is based on a Mirau-type interferometer with an adjustable optical path length difference (OPD) between a measurement path and a reference path.

Referring to FIG. 1, a source module 105 provides illumination light 110 to a beam splitter 115, which directs the illumination light 110 to a Mirau interferometric objective assembly 120. The assembly 120 includes an objective lens 125, a reference flat 130 having a reflective coating on a small central portion thereof defining a reference mirror 135, and a beam splitter 140. During operation, the objective lens 125 focuses the illumination light towards an object 145 through the reference flat 130. The object 145 is characterized by its surface height profile h(x,y), which varies over the object surface, and its complex surface structure.

The beam splitter 140 transmits a first portion of the focusing light to the object 145 to define measurement light 150 and reflects a second portion of the focusing light to the reference mirror 135 to define reference light 155. Then, the beam splitter 140 recombines the measurement light 150 reflected (or scattered) from the object 145 with the reference light 155 reflected from the reference mirror 135. The objective 125 and an imaging lens 160 image the combined light to interfere on a detector 165 (e.g. a multi-pixel camera). As the relative position of the object 145 is being scanned, the detector 165 measures the intensity of the interfering light at one or more pixels of the detector and sends that information to a computer 167 for analysis.

The scanning in the Mirau-type interferometry system 100 involves a piezoelectric transducer (PZT) 170 coupled to the Mirau interferometric objective assembly 120. The PZT 170 is configured to scan the assembly 120 as a whole relative to the object 145 along the optical axis of the objective lens 125 as denoted by the scan coordinate $\zeta$ in FIG. 1. The Mirau-type interferometry system 100 provides scanning interferometry data at each pixel of the detector 165. Alternatively, a PZT may be coupled to the object 145 rather than the assembly 120 to provide the relative motion there between, as indicated by PZT actuator 175. In yet further embodiments, the scanning may be provided by moving one or both of the reference mirror 135 and the beam splitter 140 relative to the objective lens 125 along the optical axis of the objective lens 125.

Source module 105 includes a spatially extended source 180, a telescope formed by lenses 185 and 187, and an aperture 190 positioned in the front focal plane of the lens 185 (which coincides with the back focal plane of lens 187). This arrangement images the spatially extended source 180 onto the pupil plane 195 of the Mirau interferometric objective assembly 120, which is an example of Koehler imaging. The size of the aperture 190 controls the size of the illumination field on the object 145.

For simplicity, FIG. 1 shows the measurement light 150 and the reference light 155 focusing onto particular points on the object 145 and the reference mirror 130, respectively, and subsequently interfering on a corresponding point on the detector 165. Such light corresponds to those portions of the illumination light 110 that propagate perpendicular to the pupil plane 195 of the Mirau interferometric objective assembly 120. Other portions of the illumination light 110 ultimately illuminate other points on the object 145 and the reference mirror 135, which are then imaged onto corresponding points on the detector 165.

The detector 165 is, for example, a multiple element (i.e., multi-pixel) camera to independently measure the interference between the measurement light 150 and reference light 155 corresponding to different points on the object 145 (i.e., to provide spatial resolution for the interference pattern). The optical resolution of the interferometry system 100 is given by its optical characteristics and the pixel size of the detector 165.

Because the scanning occurs in a region where the illumination light 110 is being focused onto the object 145, the scan varies the OPD depending on the angle of incidence. As a result, the OPD from the source 201 to the detector 165 between interfering portions of the measurement light 150 and reference light 155 scale differently with the scan coordinate $\zeta$ depending on the angle of the measurement light 150 incident on, and emerging from, the object 145.

This difference in how the OPD varies with the scan coordinate $\zeta$ introduces a limited coherence length of the light measured at each pixel of the detector 165. Thus, the interference signal (as a function of scan coordinate $\zeta$) is typically modulated by an envelope having a spatial coherence length on the order of $\lambda/2(NA)^2$, where $\lambda$ is the nominal wavelength of the illumination light and NA is the numerical aperture of the assembly 120. To increase the limited spatial coherence, the assembly 120 in the scanning interferometry system 100 can define a large numerical aperture NA, e.g., greater than about 0.7 (or more preferably, greater than about 0.8, or greater than about 0.9). The interference signal can also be modulated by a limited temporal coherence length associated with the spectral bandwidth of the illumination source 180. Depending on the configuration of the interferometry system 100, one or the other of these limited coherence length effects may dominate, or they may both contribute substantially to the overall coherence length.

Figure 2:
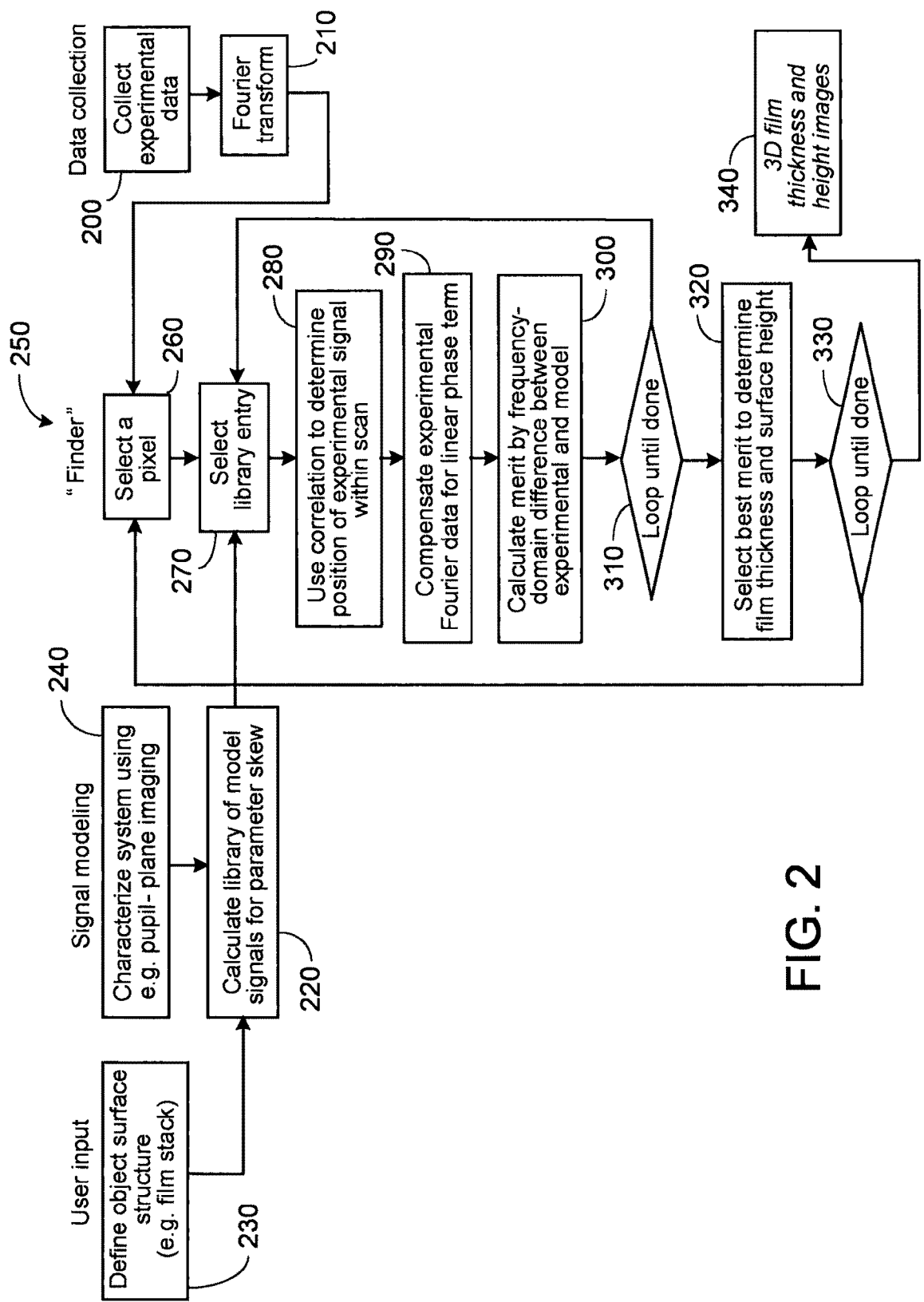
FIG. 2 is a flow chart of an interferometry method for determining a surface structure.

FIG. 2 shows an exemplary flow chart of the analysis of interferometry signal based on a surface-height offset compensation. To acquire interferometry signals for the object 145, the interferometry system 100 scans mechanically or electro-optically the optical path difference between the reference and measurement path. The measurement light 150 is directed along the measurement path to the object 145 and after reflection interferes with the reference light 155. The OPD at the beginning of the scan depends on the local surface height of the object 145. The intensity of the interfering light is detected with the detector 165. During the scan, the computer 167 records experimental intensity data $I_{ex}(x, y, \zeta)$ for each image point or camera pixel x,y in successive camera frames (step 200). Neglecting any influence of the interferometry system 100 (e.g. detector sensitivity), the experimental intensity data $I_{ex}(x, y, \zeta)$ represent the interferometry signal. For each of multiple camera pixels corresponding to different surface locations of the object 145, the computer 167 can record such an interferometry signal during the OPD scan.

Figure 3:
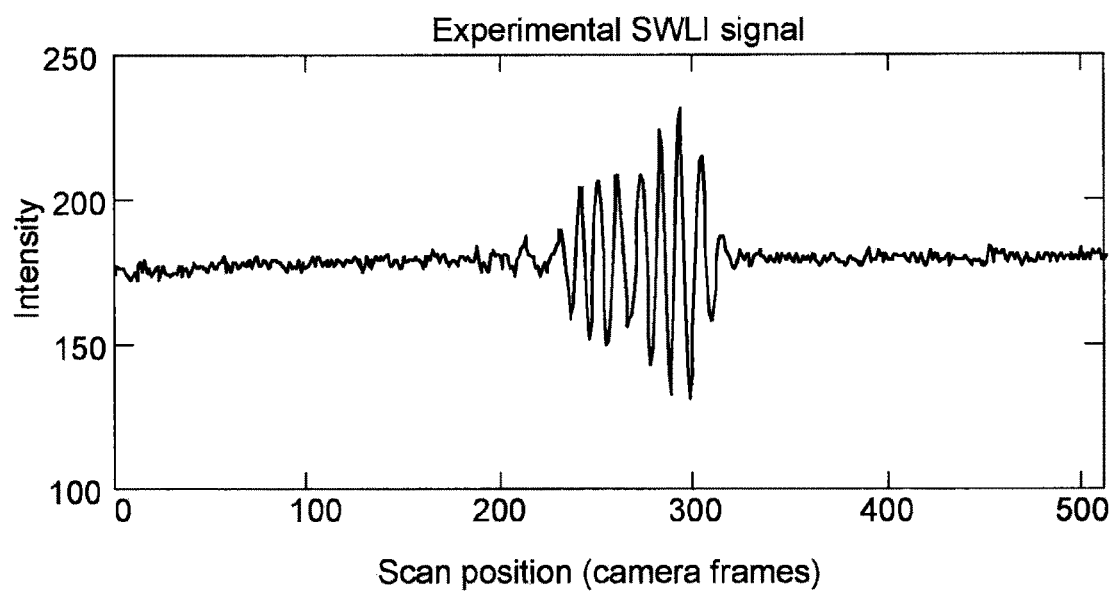
FIG. 3 shows an example of an interferometry signal.

In FIG. 3, an exemplary SWLI-signal is plotted for a single pixel. The plot shows the measured intensity as a function of the scan position $\zeta$. The SWLI-signal is detected for a Si-substrate having a $SiO_2$ thin-film. Note the two SWLI-signal comprises two overlapping signals, the one on the left for the Si-substrate and the one on the right for the top surface of the $SiO_2$ thin-film.

Next, after storing the interferometry signals as a function of OPD scan position $\zeta$, the computer performs a transformation (e.g., a Fourier Transformation) to generate a frequency-domain spectrum of the interferometry signal (step 210). This interferometry spectrum contains both magnitude and phase information as a function of the spatial frequency of the interferometry signal in the scanning dimension. An example for analyzing the interferometry signal in the frequency domain is disclosed in the commonly owned U.S. Pat. No. 5,398,113 by Peter de Groot and entitled "Method and Apparatus for Surface Topography Measurements by Spatial-Frequency Analysis of Interferograms," the contents of which are incorporated herein by reference.

The analysis of the measured interferometry signal is based on signal modeling. Specifically, one calculates and stores model signals as entries of a model library or one calculates the library entries when needed. The signal modeling can be performed with the same computer 167 or another computer (step 220).

The signal modeling is based on some user input about the object surface structure, e.g., about a film stack (step 230) and on a characterization of the interferometry system 100, e.g., by using pupil plane imaging (step 240). With that information, one calculates the entries of the library, e.g., model signals for a parameter skew of the object 145. For example, one generates a library of theoretical predictions for frequency-domain spectra for a variety of surface parameters and a system model for the interferometer. These model spectra can cover a range of possible thin film thicknesses, surface materials, and surface textures. In some embodiments, the model spectra are calculated for a constant surface height, e.g., for zero OPD. Thus, in such embodiments, the library does not contain information regarding the position of the object along the scan coordinate but contains information about the type of complex surface structure and the interaction of the object 145, the optical system, the illumination system, and detection system.

Turning now to an exemplary generation of a library of SWLI model signals, a SWLI signal is the sum of the interference signals over all the rays passing through the pupil and over all the wavelengths of the light source. Incoherent superposition allows calculating a model signal $I(L,\zeta)$ for a specific film thickness L as an inverse Fourier Transform:

$$I(L, \zeta) = \int_{-\infty}^{\infty} \rho(L, K) \exp(-iK\zeta) dk \tag{1}$$

where $\rho(L,K)$ are the Fourier components at a fringe frequencies K. A fringe frequency of K=4 cycle/micron (cycle=$2\pi$ radians) means that the intensity oscillates through four full periods for every micron of scan motion. The fringe frequencies K correspond to the angle of incidence $\Psi$ of a ray passing through the illumination pupil according to $$K=4\pi\beta/\lambda \tag{2}$$

where $\beta=\cos(\Psi)$ is the directional cosine of the incident angle $\Psi$ and $\lambda$ is one of the wavelengths within the optical spectrum of the light source. The Fourier components $\rho(L,K)$ are weighting coefficients that indicate how much of the interference effect comes from the particular combinations of incident angle $\Psi$ and wavelength $\lambda$ and give rise to a fringe frequency K according to Eq. (2). The Fourier components $\rho(L,K)$ values also include complex phase information characteristic of the object surface and of the system-level dispersion. SWLI tools have a broad range of non-zero Fourier components $\rho(L,K)$ and corresponding oscillations in the intensity data $I(L,\zeta)$. For a film-free surface, constructive interference in Eq. (1) happens only near the zero-$\zeta$ scan position.

The coefficient $\rho(L,K)$ for each fringe frequency K is proportional to a single integral over the wavenumbers k=$2\pi/\lambda$ in the source spectrum:

$$\rho(L, K > 0) = \int_{k=K/2}^{\infty} Sys(\beta, k) m^*(L, \beta, k) \frac{dk}{k^2}, \tag{3}$$

where m(L, $\beta$, k) is the object reflectivity for a thin film structure of thickness L, and the system characteristics independent of the object together are collected into a variable Sys($\beta$,k). The system characteristics, here assumed circularly symmetric, include the transmissivity t($\beta$,k) of the measurement path, the reflectivity r($\beta$,k) of the reference path, the assumed axially-symmetric distribution U($\beta$) of light in the pupil plane, and the effective optical spectrum V(k) of the light source and of the detector taken together:

$$Sys(\beta,k)=U(\beta)r(\beta,k)t^*(\beta,k)V(k) \tag{4}$$

The directional cosine $\beta$ appearing in Eq. (3) is a function of both the fringe frequency K and wavenumber k according to Eq. (2), and is linked therefore to the variable k of integration.

Figure 4:
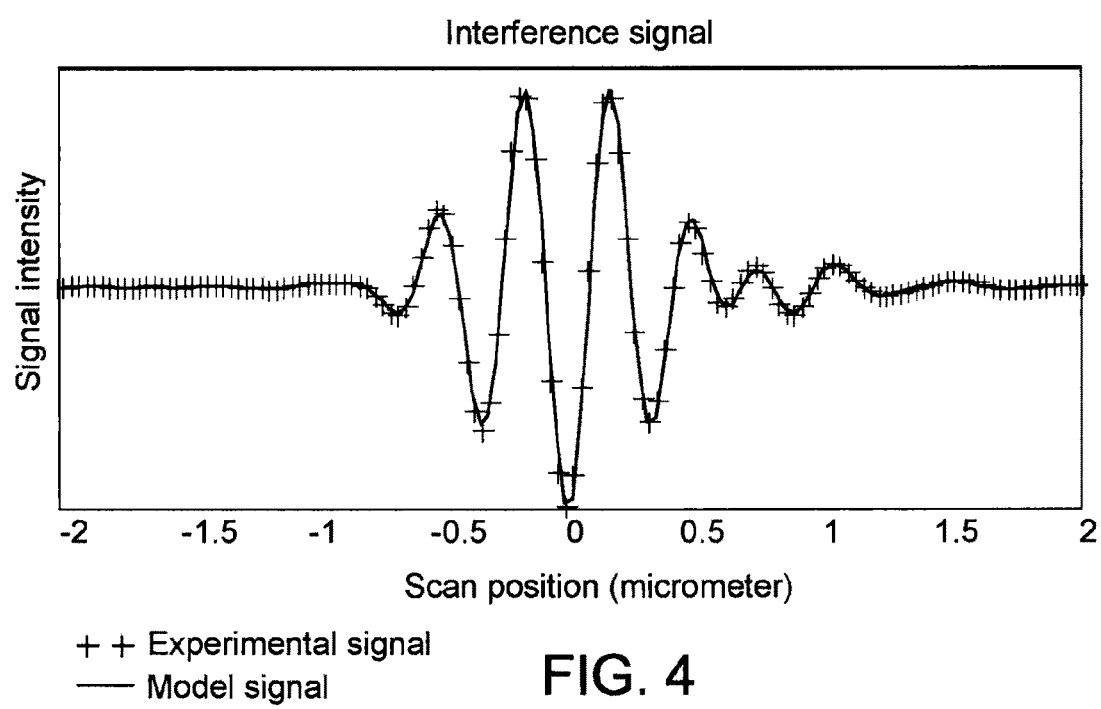
FIG. 4 shows an example of a model signal.

A system characterization or calibration determines Sys ($\beta$,k) and perhaps can be calculated as an object-independent "base" library that may be applied to object surfaces m(L, $\beta$, k) as a final step in the model signal generation. FIG. 4 illustrates the quality of the signal prediction for a solid (film-free) surface.

A method for generating model interference signals is disclosed in U.S. patent application Ser. No. 11/780,360 filed on Jul. 19, 2007 and entitled "GENERATING MODEL SIGNALS FOR INTERFEROMETRY," the contents of which are herein incorporated by reference.

Figure 5:
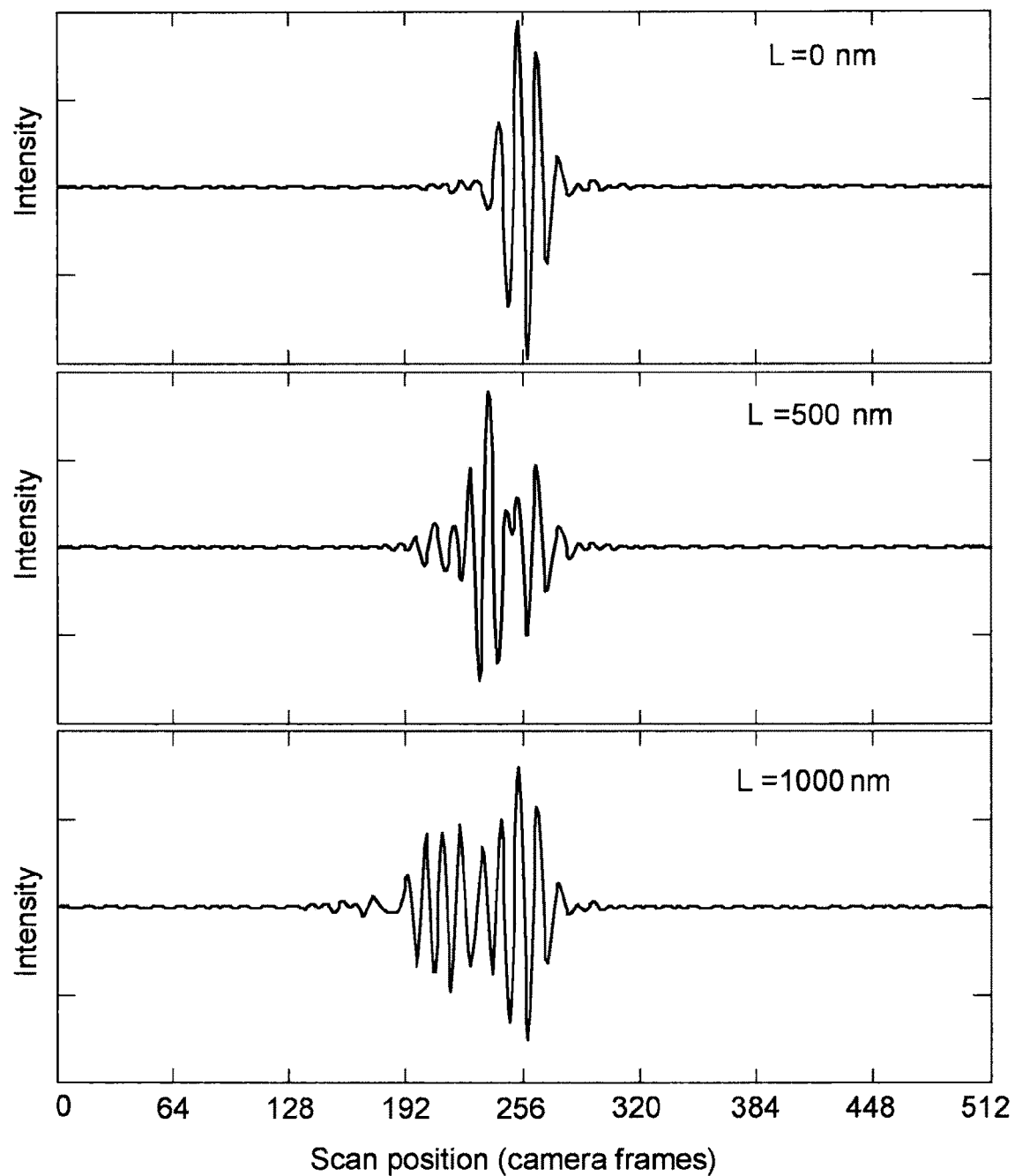
FIG. 5 shows examples of a model signal for different thin-film thicknesses.

FIG. 5 shows exemplary model signals that could be used when analyzing the experimental data of FIG. 3. For a thin-film measurement, which is an example of a common application of model-based SWLI analysis, one looks for a film thickness L assuming that the film materials are known. Thus, the film thickness L is the variable model parameter, and one approach to comparing experiment to theory is to calculate in advance a library of possible signals for comparison over a range (or skew) of film thicknesses. The model signals are then stored as their Fourier or frequency-domain equivalents ρ(L,K) calculated e.g. from Eq. (3). Of course, if the software is quick enough, one could calculate the model signals on the fly, rather than storing them. But given that potentially a large number of image pixels all with the same model parameter skew will be analyzed, it might be of advantage to use a pre-determined library. Looking at the model signals of FIG. 5, which are modeled for film-thicknesses of 0 nm, 500 nm, and 1000 nm), one could guess that the $SiO_2$ thickness contributing to the interference signal of FIG. 3 is close to 1000 nm thick.

Figure 6:
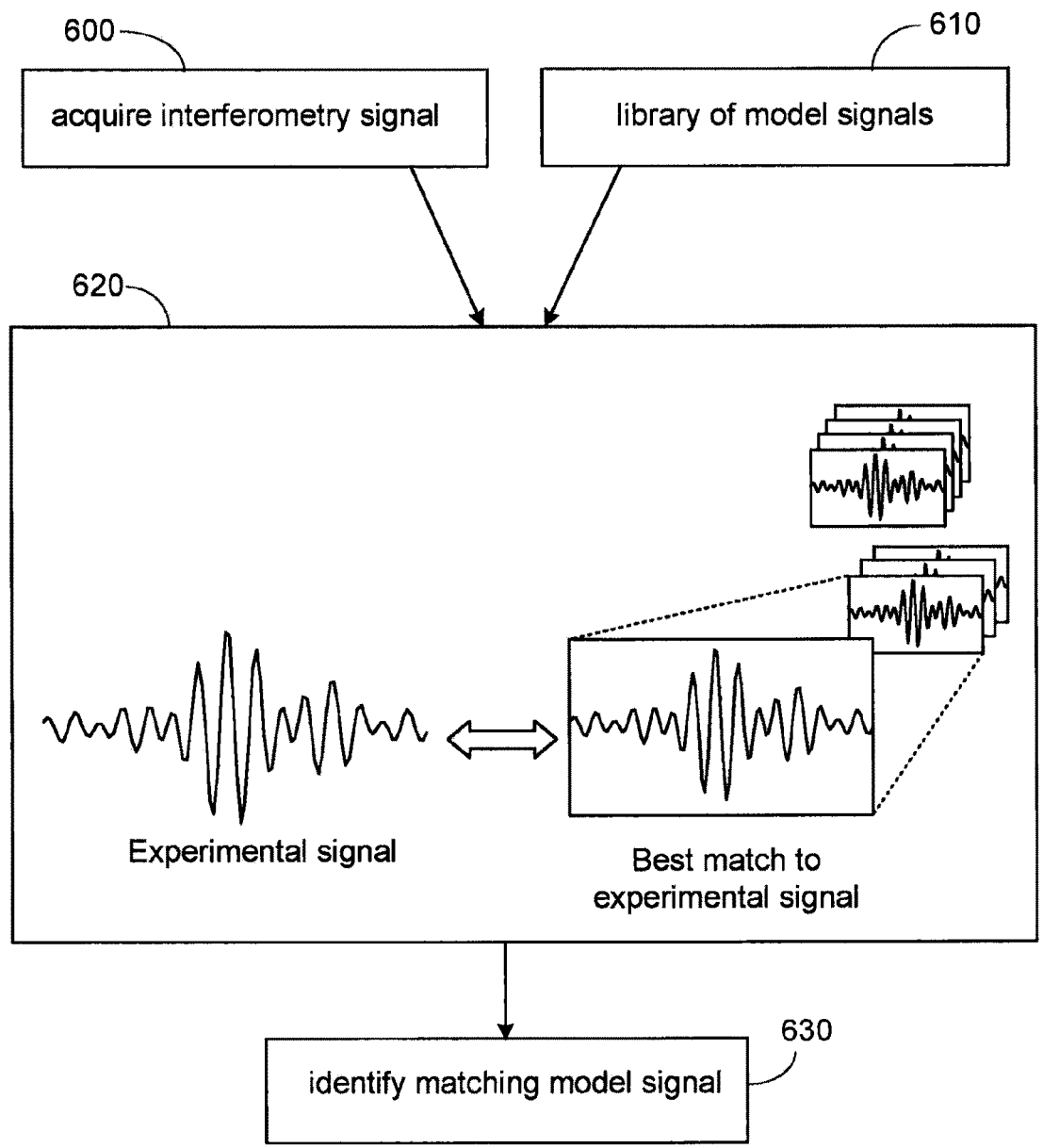
FIG. 6 is a flow chart illustrating a library search.

In a matching operation (step 250), the experimental interferometry signal is compared to the library by means of a library search that identifies a matching model signal. FIG. 6 illustrates an example flowchart of a library search that is used to analyze the object 145 for surface structure information. One acquires an interferometry signal (step 600) and generates a library of model signals (step 610). Then, one compares the interferometry signal and the model signal (step 630). Based on the comparison, one identifies the matching model signal (step 640) that is used for the determination of test object parameters characterizing the surface structure.

In the case of a thin film of unknown thickness (FIG. 3), the library for a single surface type, e.g. $SiO_2$ on Si, can range over many possible film thicknesses with, for example, the top surface height always equal to zero. Other examples of a surface structure are a surface roughness, for which the adjustable parameter may be roughness depth and/or spatial frequency, and an under-resolved grating structure.

Referring to the matching operation (step 250) shown in FIG. 2, the object 145 is analyzed in 2D on a pixel by pixel basis. Thus, one selects Fourier data for a data point (pixel) of the object (step 260). Then, one selects an entry of the library, e.g. a model signal or spectrum (step 270). Using a correlation function of the interferometry and model signal, one determines the relative position of the interferometry signal and the model signal, i.e., the surface-height offset (step 280). The surface-height offset corresponds to a phase term, based on which one compensates the interferometry signal, the model spectrum or both, e.g. in the frequency domain (step 290). Then, one calculates a height-offset compensated merit value by calculating a frequency-domain difference between the interferometry signal and the model signal (step 300).

The calculation of the merit value is repeated for the complete library or a subset of entries of the library (loop 310). Then, one identifies the "best" merit value, i.e., the library entry (or an interpolation of library entries) that best fulfills a criteria associated with the merit function. Based on that merit value and/or the associated model signal, one determines one or more test object parameters, e.g., thin film thickness and surface height (step 320).

This procedure is repeated for all pixels of interest (loop 330), and the test object parameters are presented, for example, as 3D images of the film thickness and height (step 340).

In what follows a mathematical description of the analysis is provided.

In some embodiments, one compares the model and interferometry signals in a frequency domain (e.g., Fourier-Transform domain). Because Eq. (1) is an inverse Fourier Transform, one can generate the comparable experimental Fourier coefficients $q_{ex}(x, y, K)$ from the forward transform of the experimental intensity data $I_{ex}(x, y, \zeta)$ $$q_{ex}(x, y, K) = \int_{-\infty}^{\infty} I_{ex}(x, y, \zeta)\exp(iK\zeta)d\zeta. \qquad (5)$$

The experimental coefficients $q_{ex}(x, y, K)$ contain a phase term that is a linear function of the surface height $h(x,y)$:

$$q_{ex}(x,y,K)=\rho_{ex}(x,y,K)\exp[iKh(x,y)]. \qquad (6)$$

The term $Kh(x,y)$ is the height-dependent phase slope that can complicate a direct comparison of the Fourier coefficients $q_{ex}(x, y, K)$ with theoretically predicted Fourier coefficients $\rho(L,K)$ based on surface structure alone, independent of surface height. Thus, at first one estimates $h(x,y)$ well enough to remove its phase contribution from $q_{ex}(x, y, K)$, leaving only the height-independent portion $\rho_{ex}(x, y, K)$.

Besides compensating for the height dependent phase on the experimental side, one can consider the phase on the model side or on both sides. In these cases, the phase compensation can correspond to propagating the experimental interferometry signal and the model signal to a scan position that optimizes the height independent overlap when comparing the two signals.

To determine the height dependent phase slope, one uses a correlation technique for estimating $h(x,y)$. Suppose one has a model signal spectrum $\rho(L,K)$. The correlation of the experimental and model signals is given by $$J(x, y, L, \zeta) = \int_{-\infty}^{\infty} q_{ex}(x, y, K)\rho^*(L, K)dK. \qquad (7)$$

For the case where an exact match of experiment to theory has been identified, the correlation is $$J(x, y, L, \zeta) = \int_{-\infty}^{\infty} |\rho(L, K)|^2 \exp\{iK[h(x, y) - \zeta]\}dK. \qquad (8)$$

The correlation should have a peak magnitude when $[h(x,y)-\zeta]=0$. The peak can be found by searching through the scan positions $\zeta$ to find the discrete position best $\zeta_{best}(x, y, L)$ (corresponding to a specific camera frame) that gives the peak value for $|J(x, y, L, \zeta)|$. The position best $\zeta_{best}(x, y, L)$ can be refined to a value $\zeta_{fine}(x, y, L)$ by, e.g., $2^{nd}$-order interpolation between camera frames.

Also in the case that the model signal is a not exactly the same as the interferometry signal, the correlation still allows identifying the position of a "best" overlap of model signal and interferometry signal.

Figure 7:
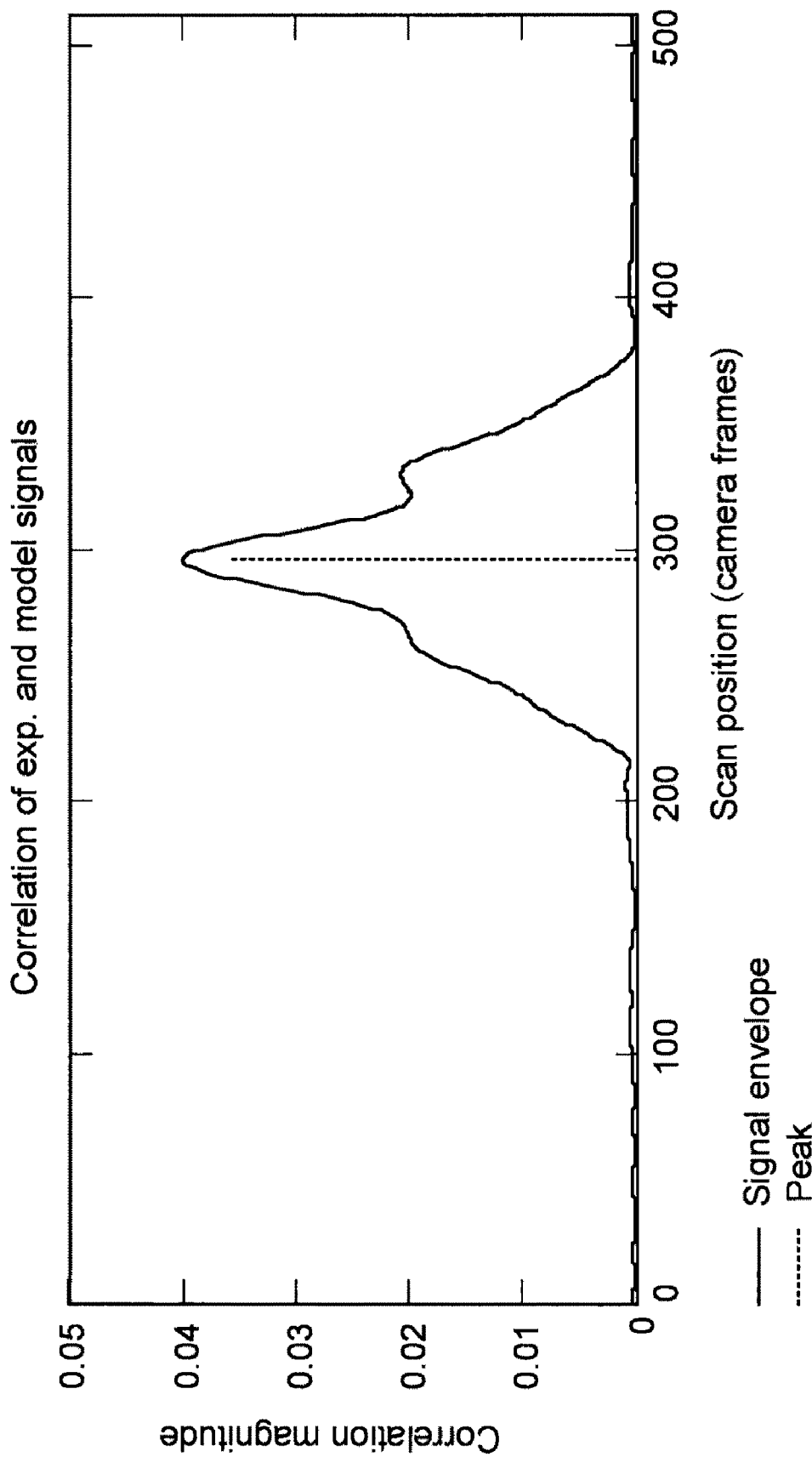
FIG. 7 is a plot of a correlation function of an interferometry signal and a model signal.

FIG. 7 shows an example correlation magnitude $|J(x, y, L, \zeta)|$ of an experimental interferometry signal and a model signal. The peak represents the position of the "best" overlap. The peak corresponds also to the local surface height when the model signal is correctly matched to the interferometry signal.

A further refinement can be based on the complex phase A of the correlation:

$$A(x,y,L)=\arg\{J[x,y,L,\zeta_{fine}(x,y,L)]\}. \qquad (9)$$

The complex phase A is associated with an overall K-independent phase gap between the model signal and interferometry signal for the cases that the signals are lined up as best as possible based on the correlation magnitude, i.e., based on the signal shape. In the ideal case, if the model signal includes any expected phase shifts related to the instrument or the surface materials, the complex phase $A(x, y, L)$ measured in this way should be zero once the correct thickness $L_{best}$ has been identified. The complex phase $A(x, y, L)$ can be preserved as a free variable to optimize the fit; but one can use the complex phase $A(x, y, L)$ also in the merit function to evaluate the quality of that fit.

Based on the refined scan position $\zeta_{fine}(x, y, L)$ giving the height offset, one can compensate the linear phase term. For example, one can calculate an experimental signal coefficients $q_{shift}$ corrected for the position within the scan and for any phase offsets with respect to the model signal:

$$q_{shift}(x,y,L,K)=q_{ex}(x,y,K)\exp[-iK\zeta_{fine}(x,y,L)-iA(x,y,L)], \qquad (10)$$

where $\zeta_{fine}(x, y, L)$ is the interpolated "best" match scan position for the correlation $|J(x, y, L, \zeta)|$, and the phase gap $A(x, y, L)$ follows from Eq. (9). If one has identified the correct thickness $L_{best}$, the phase-shifted Fourier coefficients of the interferometry signal should be $$q_{shift}(x,y,L_{best},K)=\rho_{ex}(x,y,K), \qquad (11)$$

but for all other test values of L, one can only expect that this is approximately the case.

Based on the phase compensation, one calculates a phase (height offset)-compensated merit value indicative for the quality of the fit of the model signal and the interferometry signal. A suitable measure of the quality of the match between the model signal and the interferometry signal is the least-squares difference $$\chi^2 = \sum_K [q'_{shift}(x, y, L, K) - \rho'(L, K)]^2, \qquad (12)$$

where the sum is over all of the K values for which $\rho(L,K)\neq 0$; i.e., within a frequency-domain region of interest $K_{max} \geq K \geq K_{min}$ defined by the expected signal bandwidth and max mm excluding noise and drift.

To perform this comparison directly as in Eq. (12), the model and experimental signals have been normalized for signal strength, as indicated by the primes:

$$q'_{shift}(x, y, L, K) = \frac{q_{shift}(x, y, L, K)}{\int_{K=K_{max}}^{K=K_{min}} |q_{ex}(x, y, K)| dK}, \qquad (13)$$

$$\rho'(L, K) = \frac{\rho(L, K)}{\int_{K=K_{max}}^{K=K_{min}} |\rho(L, K)| dK}. \qquad (14)$$

Figure 8:
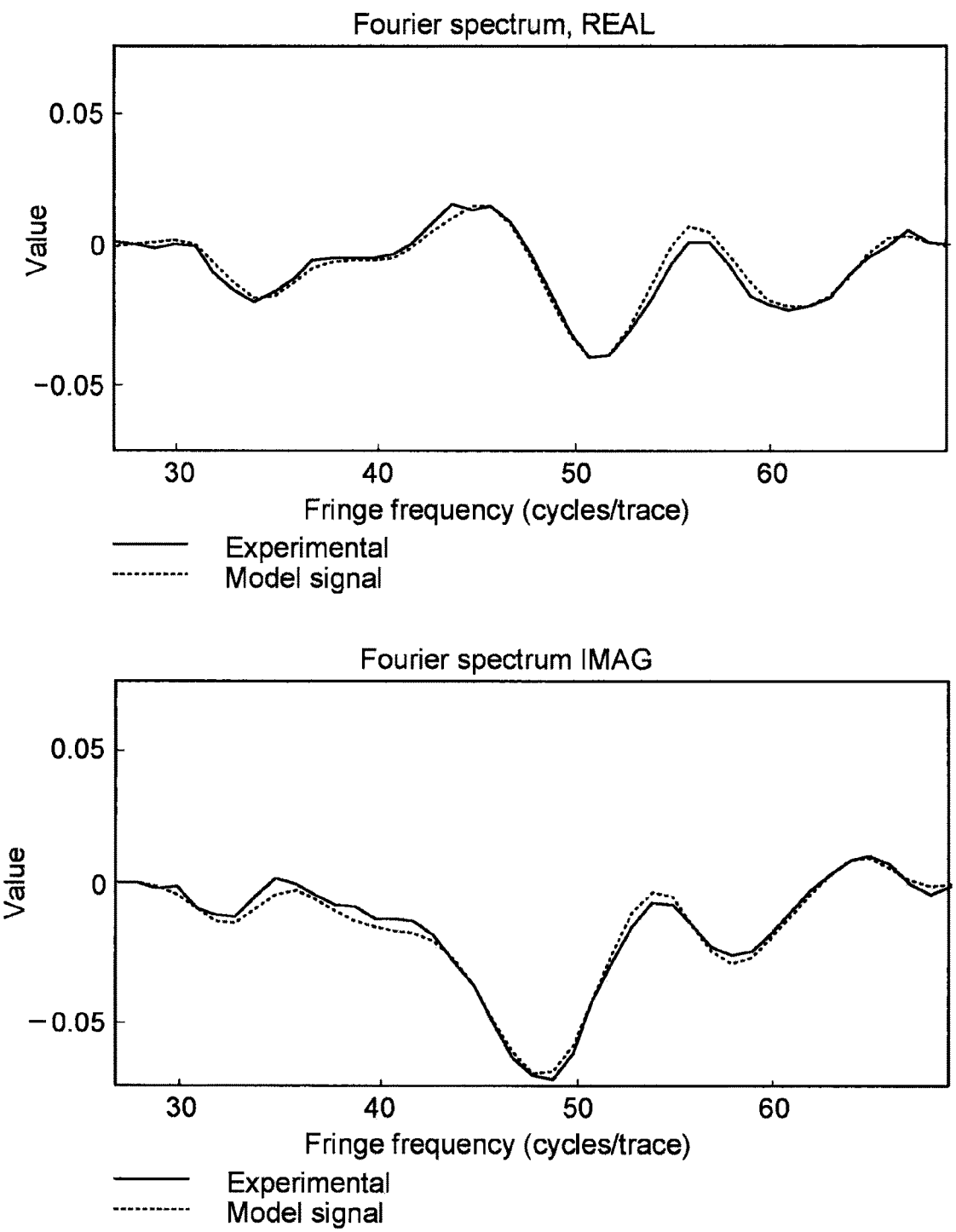
FIG. 8 shows plots of the real and imaginary parts of the Fourier spectrum for an interferometry signal and a model signal.

FIG. 8 shows a graphical comparison for the real and imaginary parts of the Fourier coefficients in the left and right plots, respectively. The oscillations of the coefficients are related to the film thickness—the thicker the film, the more rapid these oscillations are as a function of fringe frequency K. The smooth lines indicate the model spectrum $\rho'(L,K)$ and the lines (showing the underlying data) indicate the phase compensated experimental coefficients $q'_{shift}(x, y, L,K)$.

Figure 9:
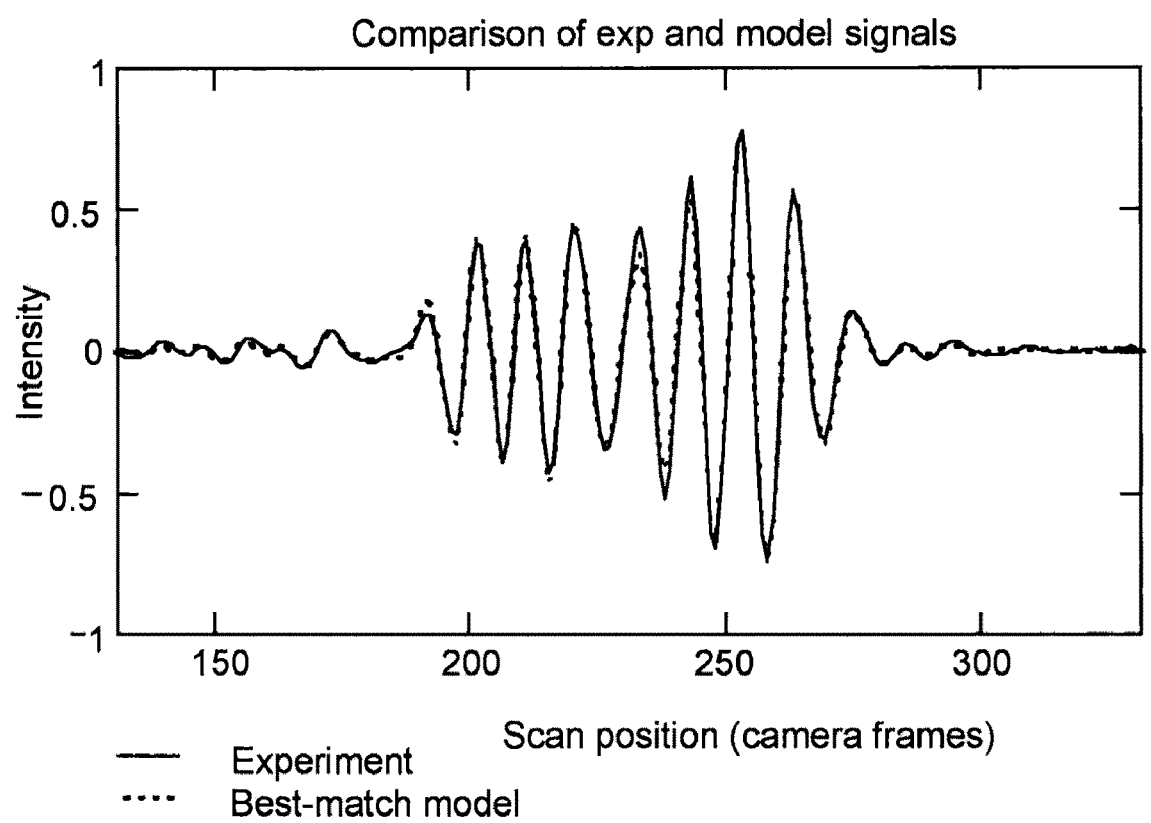
FIG. 9 shows a plot comparing an interferometry signal and a matching model signal.

FIG. 9 shows the experimental signal in the scan domain with the model signal (dotted) corresponding to the best match, as found by a Frequency-domain search. The experimental signal is much cleaner in FIG. 9 than in the original data of FIG. 3 because it is reconstructed from the region-of-interest in the frequency domain corresponding to the signal only, thus filtering out noise and low-frequency drift.

Although one can very nicely identify the best match by the minimum of the $\chi^2$-function, one may construct a merit function that is inversely proportional to the $\chi^2$-function, so that the best match is defined by a peak in a merit value distribution for the library entries. The merit function can also include other criteria, such as the phase gap $A(x, y, L)$ calculated in Eq. (9) from the complex correlation. As has been noted, in the ideal case, the phase gap $A(x, y, L)$ measured in this way should be zero at the correct thickness $L=L_{best}$; therefore, a non-zero value is a measure of the mismatch between experiment and theory. In addition, a good match should have a large correlation peak at $\zeta_{fine}$. Thus a suitable merit function is, for example, $$\Pi(x, y, L) = \frac{|J(x, y, L, \zeta_{fine})|^2}{\chi^2(x, y, L)} \left[1 - w_A \left|\frac{A(x, y, L)}{\pi}\right|\right]^2. \qquad (15)$$

One can of course construct other merit functions to optimize the robustness of the algorithm, or to use other factors such as the signal strength as merit criteria.

Figure 10:
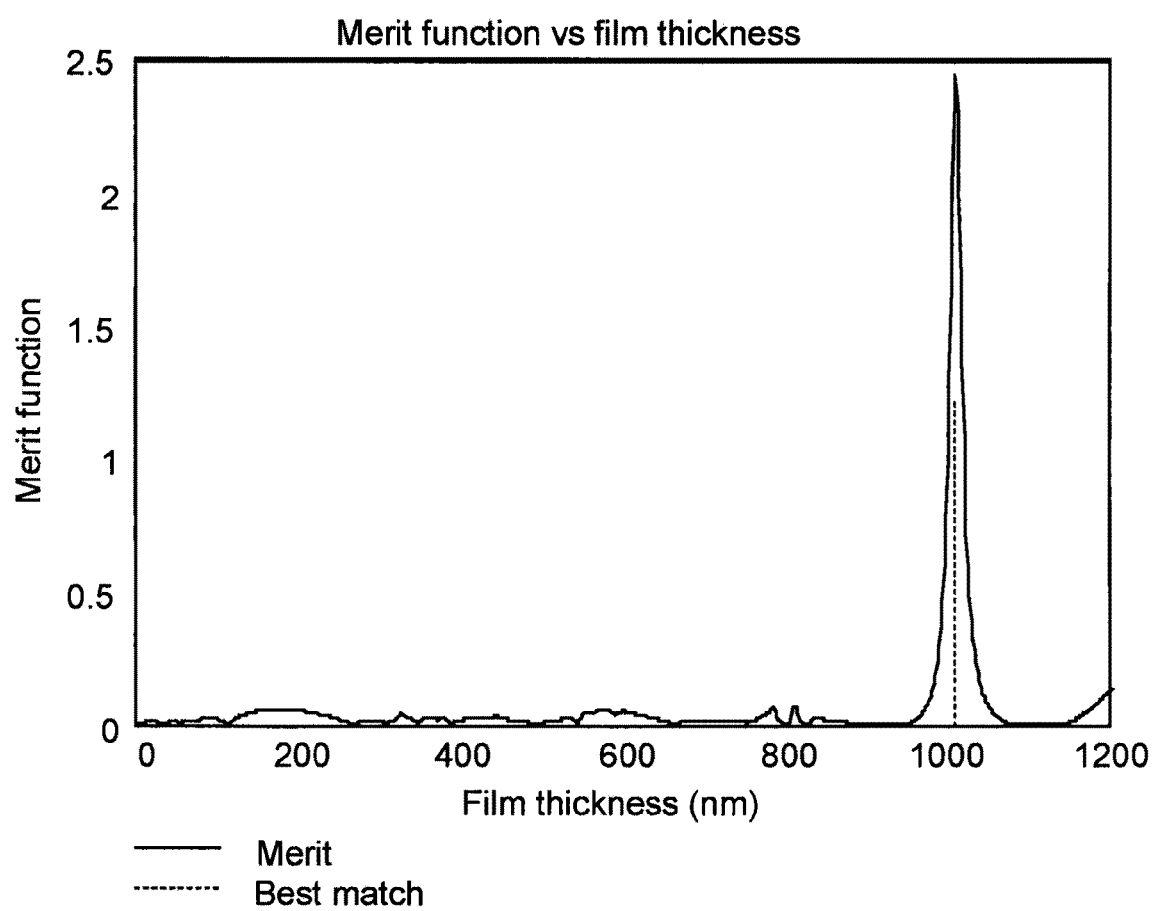
FIG. 10 is a plot of the value of a merit function for model signals for different thin-film thicknesses.

To determine the parameter characterizing surface structure, one evaluates the calculated values of the merit-function for the applied model signals. FIG. 10 shows a distribution of merit values for the example signal of FIG. 3. If the model-signal library has a small enough thickness increment, then it is sufficient to simply identify the model signal at $L=L_{best}$ that gives the highest merit-value. Otherwise, it may be useful and efficient to interpolate to $L_{fine}$ by means of a $2^{nd}$-order fit near the library value $L_{best}$. Other possibilities include interpolating the model signal itself between neighboring values, or performing a "live" search that involves calculating the model signal in real time, rather than using stored library values. An additional option is to average the merit values over multiple pixels, to improve signal to noise.

The distribution of the merit values indicates the quality of the match between the model signals for a specific film thickness ($SiO_2$ over Si) and the experimental interferometry signal. In the case of FIG. 10, the best matching model signal has been modeled for a model parameter associated with a film thickness of 1008 nm.

In some embodiments, it may be straight forward to generate top-surface height profiles because one has already calculated the necessary information during the correlation procedure. A first estimate of surface height based on the coherence peak is $$h_\Theta(x,y)=\zeta_{fine}(x,y,L_{best}), \qquad (16)$$

where the subscript $\Theta$ indicates that this height relates to the coherence or signal shape effect. A more refined estimate is given by $$h_\theta(x, y) = h_\Theta(x, y) + \frac{1}{K_0}\left\{2\pi \text{ round}\left[\frac{A(x, y, L_{best}) - \alpha}{2\pi}\right]\right\}, \qquad (17)$$

where $\alpha$ is the field average of $A(x, y, L_{best})$ over the x and y coordinates, and $K_0$ is the nominal carrier-signal frequency defined by the centroid of the square magnitudes of the Fourier coefficients for a surface without a film:

$$K_0 = \frac{\int_0^\infty K|\rho(L=0, K)|^2 dK}{\int_0^\infty |\rho(L=0, K)|^2 dK}. \tag{18}$$

Figure 11:
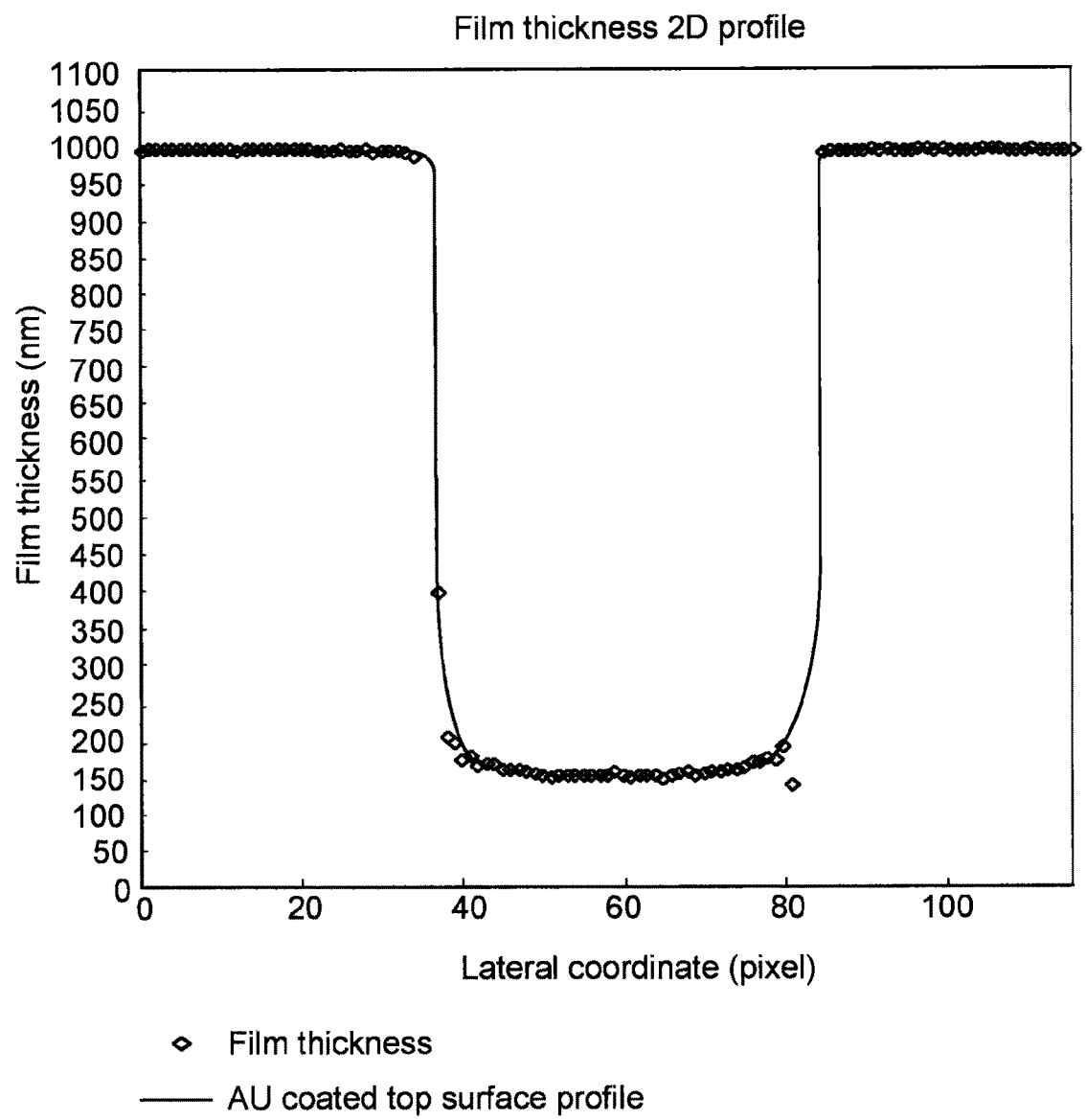
FIG. 11 shows a plot of a 2D-profile of an etched trench in a substrate with a thin-film.
Figure 12:
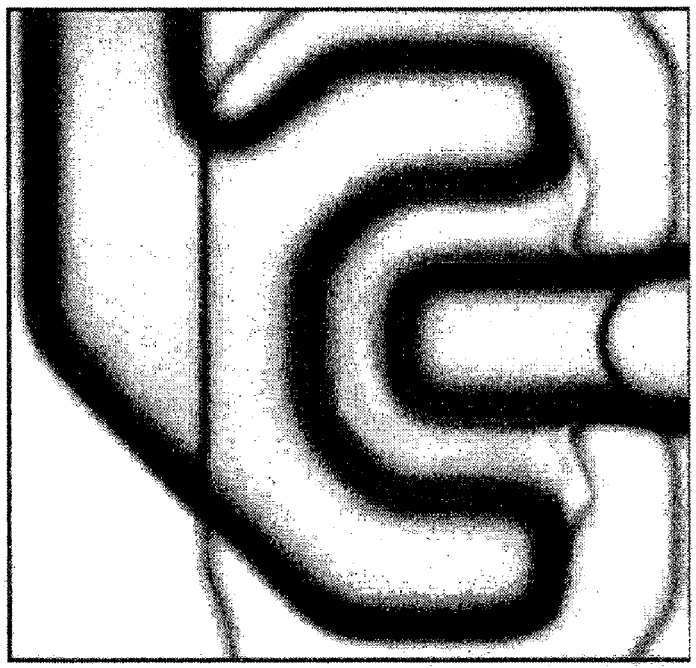
FIG. 12 shows a plot of a 3D surface profile of a TFT area for a flat-panel display.
Figure 12:
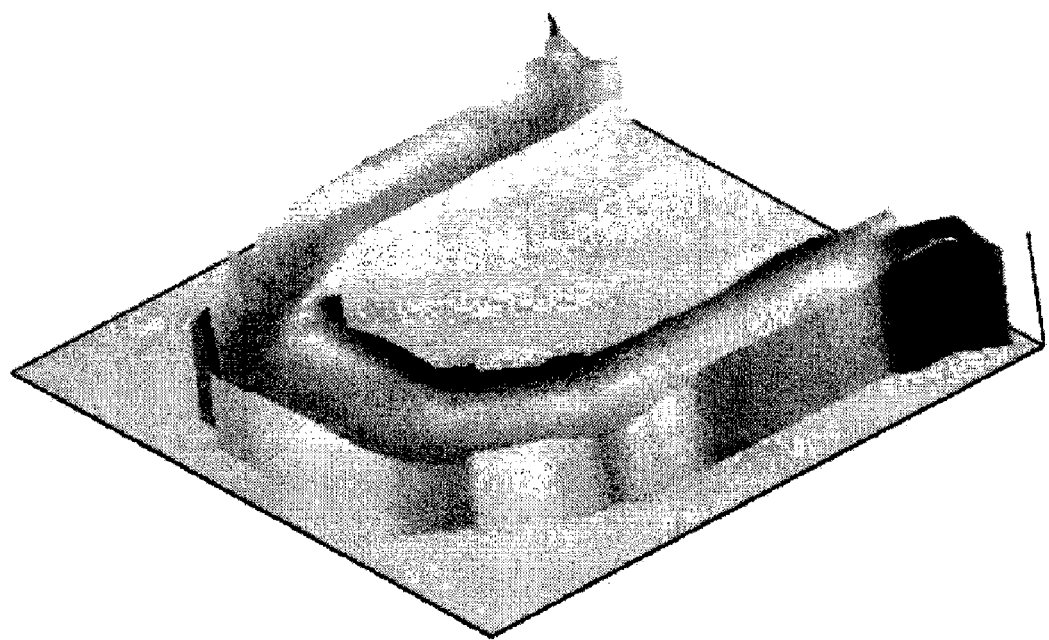

FIGS. 11 and 12 illustrate the profiling capability of the methods and systems described herein. FIG. 11 shows a 2D surface profile of a trench that has been etched into the 980-nm thick $SiO_2$ film to a depth of approximately 160 nm. Part of the trench has been coated with gold so that the top-surface profile may be measured without interference from the thin film effect. The line is the top-surface profile as measured by coating the trench with gold. The comparison in FIG. 11 is between this top-surface height profile and the measured film thickness, with an offset to the height profile to line up the curves at the top surface. The result shows a slightly deeper trench depth, which may be real (a consequence of the gold pooling at the bottom of the trench) or an artifact of the modeling. In either case, the match is quite close and illustrates <200 nm film thickness profiling to high lateral resolution.

FIG. 12 shows a 3D surface profile of a TFT area for a flat-panel display. The TFT area as shown in the 100× intensity image on the left, has a thickness range for a photoresist film in the horseshoe-shaped HT area that measures from 120 nm to 320 nm in the 3D profile on the right.

The disclosed embodiments do not depend on unwrapping the phase when one identifies the height-offset and are, therefore, generally not affected by the uncertainty that can be introduced by phase unwrapping. The uncertainty of phase unwrapping is explained in connection with FIG. 13. Some methods for analyzing an interferometry signal relay on phase unwrapping. For example, in one embodiment disclosed in U.S. Pat. No. 7,106,454, one removes the linear phase change by subtracting a linear fit to the difference in phase between the scanning interferometry signal and the model signal. Then, one analyzes the remaining non-linear phase spectrum.

Removing the phase slope by linear fitting requires that one unwraps or connects the phase data across the Fourier frequencies. Phase unwrapping removes the inevitable $2\pi$ phase uncertainties, which are generated when the phase values are calculated. However, phase unwrapping is not always easy, for example, with complex surface structures. Real phase nonlinearities associated with a thin film can have amplitudes of $\pi$ for wavelengths and angles corresponding to an anti-reflection coating.

Figure 13:
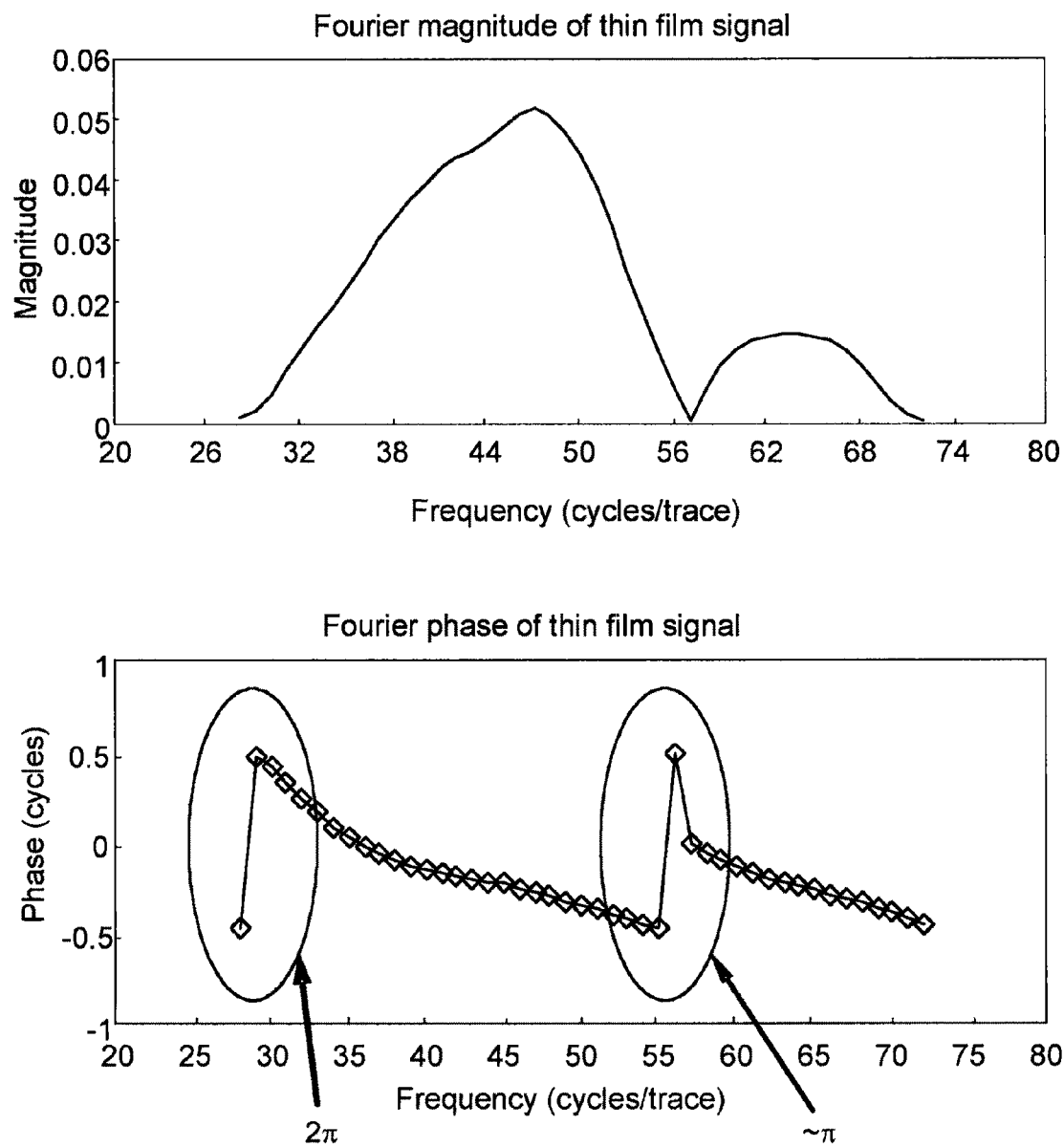
FIG. 13 shows Fourier magnitude and Fourier phase associated with a thin film interferometry signal.

In FIG. 13, the Fourier magnitude and phase are plotted over the Fourier frequency (cycles/trace) for a scanning interferometry signal of test object having a thin film of a photoresist material over molybdenum with a thickness of 508 nm.

The example of FIG. 13 illustrates the uncertainty that is present in phase unwrapping and that affects the quality of the analysis of the test object. One-cycle or $2\pi$ phase jumps are given between frequency bins 28 and 29 and between frequency bins 55 and 56. A $2\pi$ phase jump is most likely a result of the overall phase slope wrapped into the $\pm\pi$ range. The $2\pi$ phase jump at frequency bins 55 and 56 can be repaired by subtracting $2\pi$ and continuing the phase at a value of $-0.5$ cycles.

The phase jump from bin 56 to bin 57 is more complicated because it is different from bin 56 by almost exactly $\pi$. The unwrapping procedure is chaotic across such a phase step, sometimes wrapping up by $2\pi$, sometimes not. When the phase unwrapping is inconsistent, the result of the analysis is also inconsistent.

A number of embodiments have been described. Nevertheless, it will be understood that various modifications may be made without departing from the spirit and scope of the invention, some examples of which are described below.

In this disclosure, "interferometry signal" and "model signal" are often used for simplifying reasons but information derived thereof can be used in a like manner for many purposes. For example, the comparing of the interferometry signal and the model signal can be based on processed interferometry and/or model signals. For example, the interferometry signals can be digitally pre-processed, by noise suppression or correction, selection of a signal portion or a time window. Moreover, the comparing can be based on a library comparison of the interferometry signal in a frequency domain representation, e.g., a comparison of a frequency spectrum associated with the interferometry signal and a modeled frequency spectrum.

Although in the above described embodiments, the height compensation was achieved by modifying the scanning interferometry signal, one can also modify the model signal, or both, i.e., the scanning interferometry signal and the model signals. However, the modification should be such that comparing the interferometry signal and the model signal is based on signals that are associated with a common surface height. For example, the propagated optical path length in the model is adjusted to the optical path length of the interferometer such that the zero OPDs in the interferometer and the model are based on same condition for the measurement light and the test light.

Generally, the height-offset compensated merit value can be calculated based on a height-offset compensated, phase-compensated, and/or surface-height independent interferometry signal (or information derived thereof). For example, the height-offset compensated merit value can be derived in a phase-compensated spectral presentation of the interferometry signal, e.g. a Fourier spectrum.

For the comparison with a model signal, a library of model signals may be generated empirically, using sample artifacts. As another alternative, the library may use information from prior supplemental measurements of the object surface provided by other instruments, for example an ellipsometer, and any other input from a user regarding known properties of the object surface, so as to reduce the number of unknown surface parameters. Any of these techniques for library generation, theoretical modeling, empirical data, or theory augmented by supplemental measurements, may be expanded by interpolation to generate intermediate values, either as part of the library creation or in real time during a library search.

Comparing the model and the interferometry signals may be based on any of the following: a product of, or a difference between, magnitude and/or phase data in the frequency spectrum, including, e.g., the product of, or difference between, the average magnitude and the average phase, the average magnitude itself, and the average phase itself, the slope, width and/or height of the magnitude spectrum; interference contrast; data in the frequency spectrum at DC or zero spatial frequency; nonlinearity or shape of the magnitude spectrum; the zero-frequency intercept of the phase; nonlinearity or shape of the phase spectrum; and any combination of these criteria.

In some embodiments, a test object parameter is determined based on the calculated merit value. Specifically, the test object parameter can be based on a "best-matching" model signal having the best merit value, on one or more interpolated model signal derived from one or more "best-matching" model signals, and/or on interpolated model parameters associated with one or more "best-matching" model signals.

Examples of a test object parameter include parameters describing the surface structure. The surface structure can be characterized by surface-height features, which can be, for example, optically resolved with an interferometry microscope, and by features of a complex surface structure. In this specification complex surface structure includes inner structure of the test object and under-resolved surface structure that can not be optically resolved with the interferometry microscope. Examples for parameters of a surface height feature include the surface height itself. Examples for parameters of an inner structure include thin-film data (e.g., thickness, index of refraction, and number of thin film layers). Examples for parameters of an under-resolved surface structure include under-resolved feature data such as under-resolved diffraction grating structure, step height structure, and location of a step.

The test object parameter can be associated with the model signal. For example, a parameter characterizing the surface height can be determined through correlating the interferometry signal and a best matching model signal. Then, the correlation produces a peak at a scan coordinate associated to the surface height. Similarly, in the frequency domain, the surface height can be extracted using conventional FDA analysis. As an example for a complex surface feature, one can assign the thickness of a surface film that was used as a model parameter when modeling the best matching model signal as the determined thickness of a surface film of the test object.

In some cases, the comparison can be performed iteratively to further improve the results. In two dimensions, the comparison can be refined on a pixel-by-pixel or regional basis, by the creation of refined model signals relevant to the local surface type. For example, if it is found that the surface has a thin film of approximately 0.1 micron during a preliminary comparison, then the computer may generate a fine-grain library of example model parameters (thin film thickness) close to 1 micron to further refine the comparison.

In some embodiments, the analysis may be similar to that described in FIG. 2 except that the height compensated comparison between the interferometry signal and the model signals is based on information in the scan coordinate domain. The experimental signal may be characterized by a quasi-periodic carrier oscillation modulated in amplitude by an envelope function with respect to the scan coordinate. Comparing the model and the interferometry signals may then be based on any of the following: average signal strength; the shape of the signal envelope, including e.g. deviation from some ideal or reference shape such as a Gaussian; the compensated phase of the carrier signal with respect to the envelope function; the relative spacing of zero crossings and/or signal maxima and minima; values for maxima and minima and their ordering; peak value of the correlation between the interferometry and model signals, after adjusting for optimal relative scan position; and any combination of these criteria.

Based on the comparison of the interferometry signal and model signals, one can determine one or more test object parameters. The computer may then display or transmit these test object parameters describing the surface structure (complex surface structure and height information) numerically or graphically to the user or to a host system for further analysis or for data storage.

For example, using the matching model and/or the correlation function, the computer determines surface height information in addition to characteristics of the identified complex surface structure. For the case of 2D imaging, the computer can generate, for example, a three-dimensional image constructed from the height data and corresponding image plane coordinates, together with graphical or numerical display of the complex surface structure.

In some embodiments, the user may only be interested in the complex surface structure modeled by the model signals, but not in the surface height, in which case the steps for determining surface height are not performed. Conversely, the user may only be interested in surface height, but not the complex surface structure modeled by the model signals, in which case the computer compensates the experimental interferometry signal (or information derived thereof), and/or the model signal (or information derived thereof) for the contributions of the linear phase when comparing the interferometry signal and the model signal, so that the matching model and consecutively the surface height may be more accurately and more efficiently determined, but the computer needs not explicitly determine the complex surface structure or display it.

The above described analysis may be applied to a variety of surface analysis problems, including: simple thin films (in which case, for example, the variable parameter of interest may be the film thickness, the refractive index of the film, the refractive index of the substrate, or some combination thereof); multilayer thin films; sharp edges and surface features that diffract or otherwise generate complex interference effects; under-resolved surface roughness; under-resolved surface features, for example, a sub-wavelength width groove on an otherwise smooth surface; dissimilar materials (for example, the surface may comprise a combination of thin film and a solid metal, in which case the library may include both surface structure types and automatically identify the film or the solid metal by a match to the corresponding frequency-domain spectra); optical activity such as fluorescence; spectroscopic properties of the surface, such as color and wavelength-dependent reflectivity; polarization-dependent properties of the surface; deflections, vibrations or motions of the surface or deformable surface features that result in perturbations of the interference signal; and data distortions related to the data acquisition procedure, e.g. a data acquisition window that does not fully encompass the interferometry signal.

Thus, test object parameters characterizing related features can be determined and model signals can be parameterized with model parameters describing these features in the modeling process.

In some cases, the analysis may also include a system characterization, which includes, e.g. measuring one or more reference artifacts having a known surface structure and surface topography, so as to determine parameters such as system wave front error, dispersion, and efficiency that may not be included in the theoretical model.

Furthermore, the analysis may include an overall calibration, which includes e.g., measuring one or more reference artifacts to determine the correlation between measured surface parameters, such as film thickness as determined by the library search, and the values for these parameters as determined independently, e.g. by ellipsometric analysis.

The interferometry system may include any of the following features: a spectrally narrow-band light source with a high numerical aperture (NA) objective; a spectrally broad band light source; a combination of a high-NA objective and a spectrally broadband source; an interferometric microscope objective, including oil/water immersion and solid immersion types, in e.g. Michelson, Mirau or Linnik geometries; a sequence of measurements at multiple wavelengths; unpolarized light; and polarized light, including linear, circular, or structured. For example, structured polarized light may involve, for example, a polarization mask, generating different polarizations for different segments of the illumination or imaging pupils, so as to reveal polarization-dependent optical effects attributable to surface characteristics. The interferometer may also include the overall system calibration, described above.

In other embodiments, a source module may include an arrangement in which a spatially extended light source is imaged directly onto the test object, which is known as critical imaging.

In some embodiments, the limited coherence length of the light used to generate the scanning interferometry signal is based on a white light source, or more generally, a broadband light source. In other embodiments, the light source may be monochromatic, and the limited coherence length can result from using a high numerical aperture (NA) for directing light to, and/or receiving light from, the test object. The high NA causes light rays to contact the test surface over a range of angles, and generates different spatial frequency components in the recorded signal when the OPD is scanned. In yet further embodiments, the limited coherence can result from a combination of both effects.

The origin of the limited coherence length may also be a physical basis for there being information in the scanning interferometry signal. Specifically, the scanning interferometry signal contains information about complex surface structure because it is produced by light rays contacting the test surface with many different wavelengths and/or at many different angles.

To provide ellipsometry measurements, the interferometry system may include a fixed or variable polarizer in the pupil plane. Referring to FIG. 1, the Mirau-type interferometry system 100 can include polarization optics 197 in the pupil plane to select a desired polarization for the light incident on, and emerging from the test sample. Furthermore, the polarization optics may be reconfigurable to vary the selected polarization. The polarization optics may include one or more elements including polarizers, waveplates, apodization apertures, and/or modulation elements for selecting a given polarization. Furthermore, the polarization optics may be fixed, structured or reconfigurable, for the purpose of generating data similar to that of an ellipsometer. For example, a first measurement with a radially-polarized pupil for s polarization, followed by a radially-polarized pupil for p polarization. In another example, one may use an apodized pupil plane with linearly polarized light, e.g., a slit or wedge, which can be rotated in the pupil plane so as to direct any desired linear polarization state to the object, or a reconfigurable screen such as a liquid crystal display.

In further embodiments, polarization optics may be positioned elsewhere in the apparatus. For example, linear polarization can be achieved anywhere in the system.

Alternative configurations may allow the use of apertures, polarizers, wavelength filters, or other devices at or near the pupil plane 195 of the interferometry system so as to isolate various azimuthal angles, positions within the pupil plane, polarizations etc., either statically or dynamically.

For example, to analyze the test object with various polarization states, one can use polarizing elements e.g. in the illumination or imaging planes. These elements may be electro-optically actuated and operate at high speed, again providing hundreds of measurements per second because of the high-speed data acquisition afforded by the single-detector geometry.

Alternatively, or in addition, one can apply or select multiple wavelengths by using a filtered light source and multiple data acquisitions. The filtering of wavelengths may be performed by spectroscopic means, tunable-wavelength interference filters, a second interferometer, an acousto-optic tunable filter, switchable light sources such as multiple lasers operated in sequence, or any other device or combination of devices.

Alternative configurations may allow high-speed data acquisition, which is made possible by a single or small number of detector elements near the image plane, allowing for rapid, repetitive measurements as needed to accommodate averaging or sequential changes in the instrument configuration, e.g., sequencing through a range of wavelengths.

Among other applications, the techniques described above can be applied to process control in semiconductor manufacturing. An example of this is in-process monitoring of critical dimensions (CDs), which is central to the fabrication of many high-technology components on the micron and nanometer scales. Examples include semiconductor IC processes such as transistor and logic creation, as well as copper-damascened connections. Defined broadly, CDs include lateral dimensions, etch depth, film thickness, step height, sidewall angle and related physical dimensions that influence the performance of semiconductor devices. CD metrology provides process control and defect detection that occur in the course of manufacturing, especially as a result of processes such as etching, polishing, cleaning and patterning. In addition, the basic measurement capabilities implied by CD metrology have broad application outside of Semiconductor IC manufacturing, including e.g. displays, nanostructures, and diffractive optics.

For example, scanning interferometry measurements can be used for non-contact surface topography measurements semiconductor wafers during chemical mechanical polishing (CMP) of a dielectric layer on the wafer. CMP is used to create a smooth surface for the dielectric layer, suitable for precision optical lithography. Based on the results of the interferometric topography methods, the process conditions for CMP (e.g., pad pressure, polishing slurry composition, etc.) can be adjusted to keep surface non-uniformities within acceptable limits.

It is to be further understood that, because some of the constituent system components and method steps depicted in the accompanying figures can be implemented in software, the actual connections between the systems components (or the process steps) may differ depending upon the manner in which the disclosed method is programmed. Given the teachings provided herein, one of ordinary skill in the related art will be able to contemplate these and similar implementations or configurations of the disclosed systems and methods.

For example, the numerical and symbolic steps described herein can be converted into a digital program executed, e.g., on a digital signal processor according to methods well known in the art. The digital program can be stored on a computer readable medium such as a hard disk and can be executable by a computer processor. Alternatively, the appropriate steps can be converted into a digital program that is hardwired into dedicated electronic circuits within the processor that executes the steps. Methods for generating such dedicated electronic circuits based on a given numerical or symbolic analysis procedure are also well known in the art.

Exemplary Applications

As discussed previously, the above-described systems and methods can be applied to a variety of surface analysis problems. A description of certain exemplary applications follows.

Semiconductor Processing

The systems and methods described above can be used in a semiconductor process for tool specific monitoring or for controlling the process flow itself. In the process monitoring application, single/multi-layer films are grown, deposited, polished, or etched away on unpatterned Si wafers (monitor wafers) by the corresponding process tool and subsequently the thickness and/or optical properties are measured using the interferometry system employing the scan error correction technique disclosed herein. The average, as well as within wafer uniformity, of thickness (and/or optical properties) of these monitor wafers are used to determine whether the associated process tool is operating with targeted specification or should be retargeted, adjusted, or taken out of production use.

In the process control application, latter single/multi-layer films are grown, deposited, polished, or etched away on patterned Si, production wafers by the corresponding process tool and subsequently the thickness and/or optical properties are measured with the interferometry system employing the scan error correction technique disclosed herein. Production measurements used for process control typical include a small measurement site and the ability to align the measurement tool to the sample region of interest. This site may consists of multi-layer film stack (that may itself be patterned) and thus requires complex mathematical modeling in order to extract the relevant physical parameters. Process control measurements determine the stability of the integrated process flow and determine whether the integrated processing should continue, be retargeted, redirected to other equipment, or shut down entirely.

Specifically, for example, the interferometry systems disclosed herein can be used to monitor the following equipment: diffusion, rapid thermal anneal, chemical vapor deposition tools (both low pressure and high pressure), dielectric etch, chemical mechanical polishers, plasma deposition, plasma etch, lithography track, and lithography exposure tools. Additionally, the interferometry system disclosed herein can be used to control the following processes: trench and isolation, transistor formation, as well as interlayer dielectric formation (such as dual damascene).

Copper Interconnect Structures and Chemical Mechanical Polishing

It is becoming common among chip makers to use the so-called 'dual damascene copper' process to fabricate electrical interconnects between different parts of a chip. This is an example of a process which may be effectively characterized using a suitable surface topography system. The dual damascene process may be considered to have six parts: (1) an interlayer dielectric (ILD) deposition, in which a layer of dielectric material (such as a polymer, or glass) is deposited onto the surface of a wafer (containing a plurality of individual chips); (2) chemical mechanical polishing (CMP), in which the dielectric layer is polished so as to create a smooth surface, suitable for precision optical lithography, (3) a combination of lithographic patterning and reactive ion etching steps, in which a complex network is created comprising narrow trenches running parallel to the wafer surface and small vias running from the bottom of the trenches to a lower (previously defined) electrically conducting layer, (4) a combination of metal deposition steps which result in the deposition of copper trenches and vias, (5) a dielectric deposition step in which a dielectric is applied over the copper trenches and vias, and (6) a final CMP step in which the excess copper is removed, leaving a network of copper filled trenches (and possibly vias) surrounded by dielectric material.

Figure 14A:
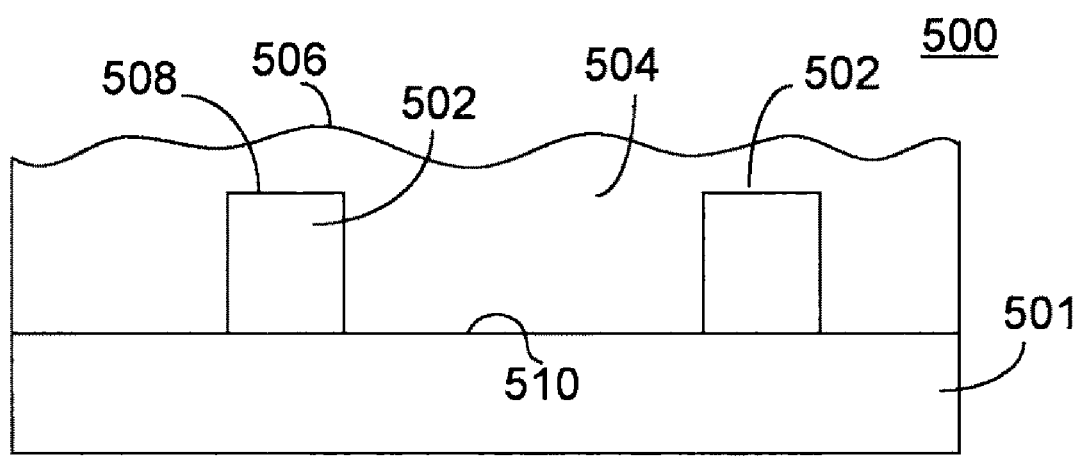
FIG. 14A is a schematic showing a device exemplary of the film structure resulting from the deposition of a dielectric over copper features deposited on a substrate.

Referring to FIG. 14A, a device 500 is exemplary of the film structure resulting from the deposition of a dielectric 504 over copper features 502 deposited on a substrate 501. The dielectric 504 has a non-uniform outer surface 506 exhibiting height variations therealong. Interference signals obtained from device 500 can include interference patterns resulting from surface 506, an interface 508 between copper features 502 and dielectric 504, and an interface 510 between substrate 501 and dielectric 504. The device 500 may include a plurality of other features that also generate interference patterns.

Figure 14B:
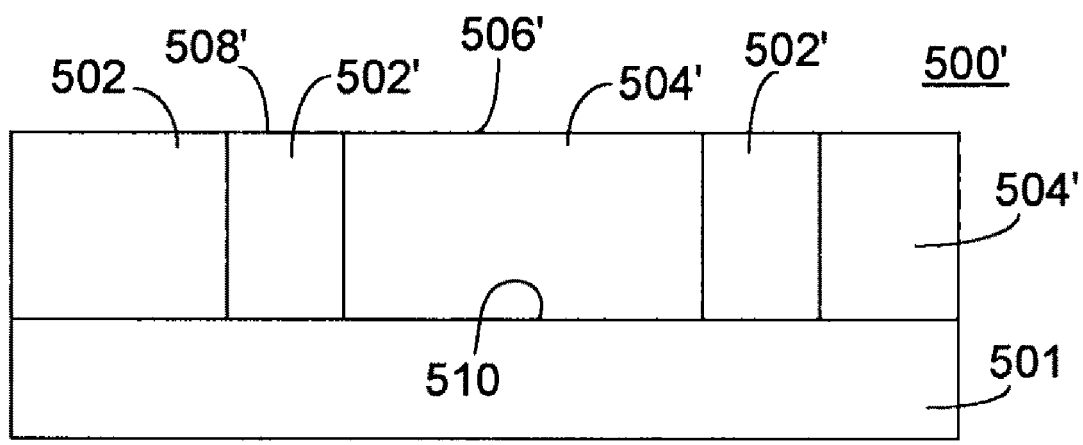
FIG. 14B is a schematic diagram of the device shown in FIG. 14A after undergoing chemical mechanical processing.

Referring to FIG. 14B, a device 500' illustrates the state of device 500 after the final CMP step. The upper surface 506 has been planarized to a surface 506', and interface 508 may now be exposed to the surroundings. Interface 510 at the substrate surface remains intact. Device performance and uniformity depends critically on monitoring the planarization of surface 504. It is important to appreciate that the polishing rate, and therefore the remaining copper (and dielectric) thickness after polishing, depends strongly and in a complex manner on the polishing conditions (such as the pad pressure and polishing slurry composition), as well as on the local detailed arrangement (i.e., orientation, proximity and shape) of copper and surrounding dielectric regions. Hence, portions of surface 506 over copper elements 502 may etch at different rates than other portions of surface 506. Additionally, once interface 508 of copper elements 502 is exposed, the dielectric and copper elements may exhibit different etch rates.

This 'position dependent polishing rate' is known to give rise to variable surface topography on many lateral length scales. For example, it may mean that chips located closer to the edge of a wafer on aggregate are polished more rapidly than those located close to the center, creating copper regions which are thinner than desired near the edges, and thicker than desired at the center. This is an example of a 'wafer scale' process nonuniformity—i.e., one occurring on length scale comparable to the wafer diameter. It is also known that regions which have a high density of copper trenches polish at a higher rate than nearby regions with low copper line densities. This leads to a phenomenon known as 'CMP induced erosion' in the high copper density regions. This is an example of a 'chip scale' process non-uniformity—i.e., one occurring on a length scale comparable to (and sometimes much less than) the linear dimensions of a single chip. Another type of chip scale nonuniformity, known as 'dishing', occurs within single copper filled trench regions (which tend to polish at a higher rate than the surrounding dielectric material). For trenches greater than a few microns in width dishing may become severe with the result that affected lines later exhibit excessive electrical resistance, leading to a chip failure.

CMP induced wafer and chip scale process nonuniformities are inherently difficult to predict, and they are subject to change over time as conditions within the CMP processing system evolve. To effectively monitor, and suitably adjust the process conditions for the purpose of ensuring that any non-uniformities remain within acceptable limits, it is important for process engineers to make frequent non-contact surface topography measurements on chips at a large number and wide variety of locations. This is possible using embodiments of the interferometry methods and systems described above.

In some embodiments one or more spatial properties, e.g., the topography of surface 506 and/or the thickness of dielectric 504, are monitored by obtaining low coherence interference signals from the structure before and/or during CMP. Based on the spatial properties, the polishing conditions can be changed to achieve the desired planar surface 506'. For example, the pad pressure, pad pressure distribution, polishing agent characteristics, solvent composition and flow, and other conditions can be determined based on the spatial properties. After some period of polishing, the spatial property can again be determined and the polishing conditions changed as needed. The topography and/or thickness is also indicative of the end-point at which, e.g., surface 504' is achieved. Thus, the low coherence interference signals can be used to avoid depressions caused by over polishing different regions of the object. The low coherence interference methods and systems are advantageous in this respect because spatial properties of the device, e.g., the relative heights of the surface of the dielectric (a) over copper elements 502 and (b) over substrate surface 510 but adjacent copper elements 502 can be determined even in the presence of the multiple interfaces.

Photolithography

Figure 15A:
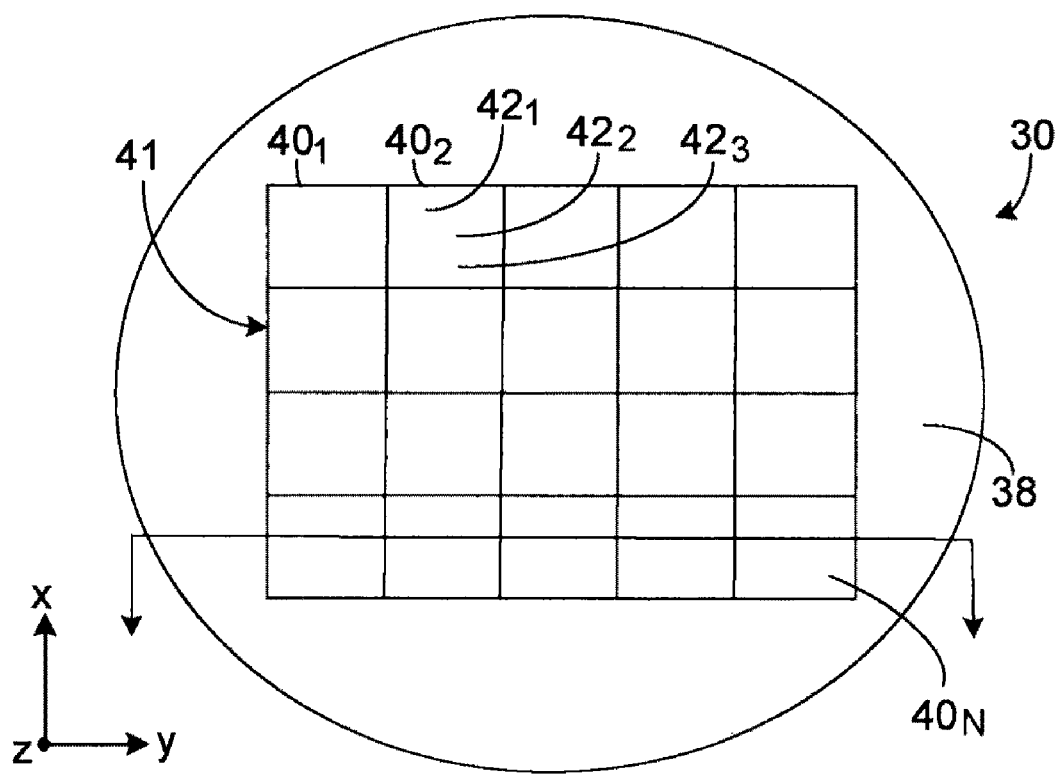
FIG. 15A is a schematic diagram showing a top down view of an object which includes a substrate, e.g., a wafer, and an overlying layer, e.g., photoresist layer.
Figure 15B:
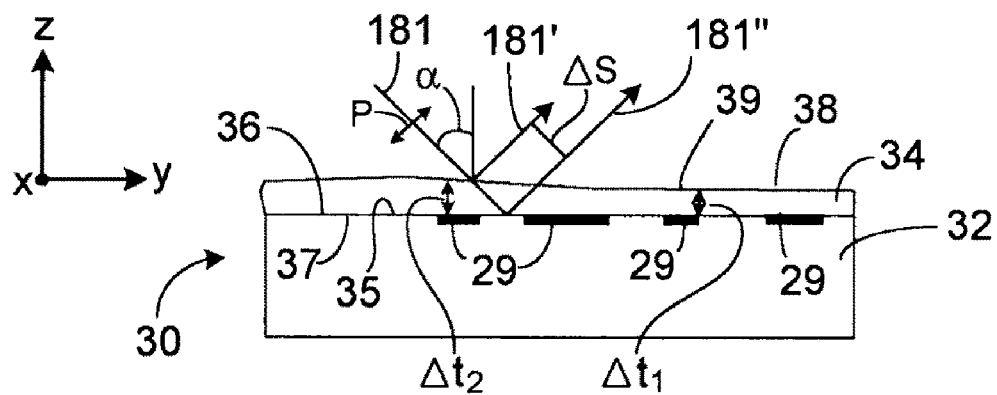
FIG. 15B is a schematic diagram showing a side on view of the object.

In many microelectronics applications, photolithography is used to pattern a layer of photoresist overlying a substrate, e.g., a silicon wafer. Referring to FIGS. 15A and 15B, an object 30 includes a substrate, e.g., a wafer, 32 and an overlying layer, e.g., photoresist layer 34. Object 30 includes a plurality of interfaces as occur between materials of different refractive index. For example, an object-surroundings interface 38 is defined where an outer surface 39 of photoresist layer 34 contacts the environment surrounding object 30, e.g., liquid, air, other gas, or vacuum. A substrate-layer interface 36 is defined between a surface 35 of wafer 32 and a bottom surface 37 of photoresist layer 34. Surface 35 of the wafer may include a plurality of patterned features 29. Some of these features have the same height as adjacent portions of the substrate but a different refractive index. Other features may extend upward or downward relative to adjacent portions of the substrate. Accordingly, interface 36 may exhibit a complex, varying topography underlying the outer surface of the photoresist.

A photolithography apparatus images a pattern onto the object. For example, the pattern may correspond with elements of an electronic circuit (or the negative of the circuit). After imaging, portions of the photoresist are removed revealing the substrate underlying the removed photoresist. The revealed substrate can be etched, covered with deposited material, or otherwise modified. Remaining photoresist protects other portions of the substrate from such modification.

To increase manufacturing efficiencies, more than one device is sometimes prepared from a single wafer. The devices may be the same or different. Each device requires that a subset of the wafer be imaged with a pattern. In some cases, the pattern is sequentially imaged onto different subsets. Sequential imaging can be performed for several reasons. Optical aberrations can prevent achieving adequate pattern focus quality over larger areas of the wafer. Even in the absence of optical aberrations, the spatial properties of the wafer and photoresist may also prevent achieving adequate pattern focus over large areas of the wafer. Aspects of the relationship between the spatial properties of the wafer/resist and focus quality are discussed next.

Referring back to FIG. 15B, object 30 is shown with a number N subsets $40_i$, each smaller than a total area 41 the object to be imaged. Within each subset $40_i$, spatial property variations, e.g., height and slope variations of the wafer or photoresist, are typically smaller than when taken over the total area 41. Nonetheless, the wafer or photoresist of different subsets $40_i$ typically have different heights and slopes. For example, layer 34 exhibits thicknesses $\Delta t_1$ and $\Delta t_2$, which vary the height and slope of surface 39. Thus, each subset of the object may have a different spatial relationship with the photolithography imager. The quality of focus is related to the spatial relationship, e.g., the distance between the object and the photolithography imager. Bringing different subsets of the object into proper focus may require relative repositioning of the object and imager. Because of the object height and slope variations, proper subset focus cannot be achieved solely by determining the position and orientation of the object with respect to a portion of the object that is remote to the imaged subset, e.g., a side 43 of the object.

Proper focus can be achieved by determining a spatial property of an object within a subset of the object to be imaged (or otherwise processed). Once the position of the subset has been determined, the object (and/or a portion of the photolithography imager) can be moved, e.g., translated, rotated, and/or tilted, to modify the position of the subset with respect to a reference, e.g., a portion of the photolithography imager. The determination and movement (if necessary) can be repeated for each subset to be imaged.

The determination of the spatial property of the subset can include determining a position and/or height of one or more points of an outer surface of a thin layer of the object, the one or more points lying within the subset of the object to be imaged. For example, the position and orientation of the outer surface 39 of subset $40_2$ (FIG. 15A) can be determined based upon the positions of points $42_1$-$42_3$ within the subset. The determination of the spatial property of the subset to be imaged can include using an interferometer to illuminate the subset with light and detecting an interference signal including light reflected from the illuminated subset. In some embodiments, a plurality of subsets are simultaneously imaged with light to obtain a plurality of interference signals. Each interference signal is indicative of one or more spatial properties of a subset. Thus, the interference signals can be used to prepare an image indicative of the topography of the object over a plurality of the subsets. During photolithography of the subsets, the wafer is positioned based upon the topography of the individual subsets as determined from the plurality of interference signals. Hence, each subset can be positioned for optimum focus with respect to the photolithography apparatus.

Detecting an interference signal from each subset of an object to be imaged can include detecting light reflected from the subset and reference light over an OPD range that is at least as large as a coherence length of the detected light. For example, the light may be detected at least over its coherence length. In some embodiments, the interferometer is configured so that the light reflected from the illuminated subset is dominated by light reflected from either an outer interface (such as outer surface 39) or an inner interface (such as interface 36). In some embodiments, a spatial property of an object is determined based on only a portion of the interference signal. For example, if the interference signal includes two or more overlapping interference patterns, a spatial property of the object can be determined based upon a portion of one of the interference patterns that is dominated by contributions from a single interface of the object.

Solder Bump Processing

Figure 16A:
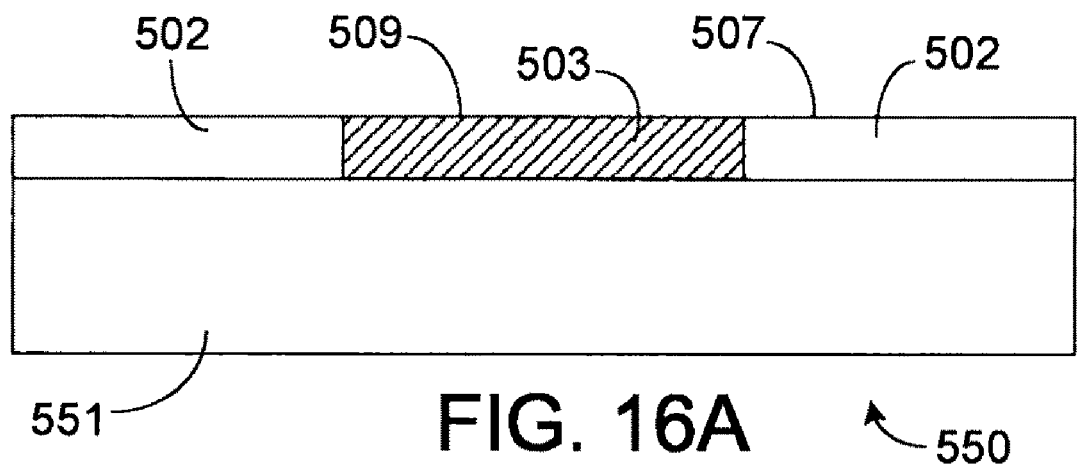
FIG. 16A is a schematic diagram of a structure suitable for use in solder bump processing.
Figure 16B:
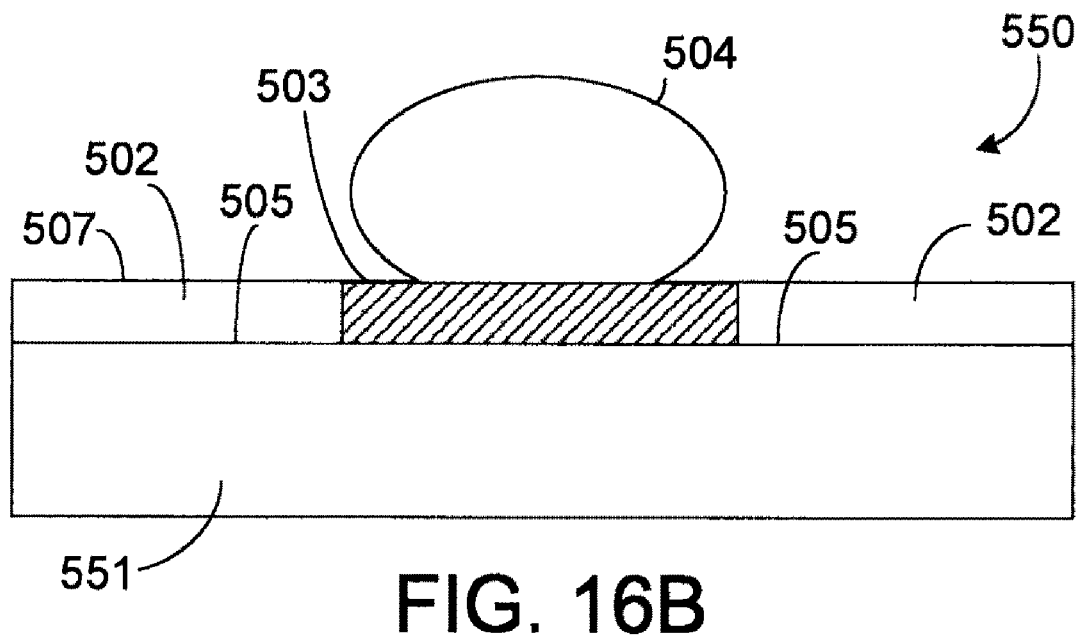
FIG. 16B is a schematic diagram of the structure from FIG. 16A after solder bump processing has occurred.

Referring to FIGS. 16A and 16B, a structure 1050 is exemplary of a structure produced during solder bump processing. Structure 1050 includes a substrate 1051, regions 1002 non-wettable by solder, and a region 1003 wettable by solder. Regions 1002 have an outer surface 1007. Region 1003 has an outer surface 1009. Accordingly, an interface 1005 is formed between regions 1002 and substrate 1001.

During processing a mass of solder 1004 is positioned in contact with wettable region 1003. Upon flowing the solder, the solder forms a secure contact with the wettable region 1003. Adjacent non-wettable regions 1002 act like a dam preventing the flowed solder from undesirable migration about the structure. It is desirable to know spatial properties of the structure including the relative heights of surfaces 1007, 1009 and the dimensions of solder 1004 relative to surface 1002. As can be determined from other discussions herein, structure 1050 includes a plurality of interfaces that may each result in an interference pattern. Overlap between the interference patterns prevents accurate determinate of the spatial properties using known interference techniques. Application of the systems and methods discussed herein allow the spatial properties to be determined.

Spatial properties determined from structure 1050 can be used to change manufacturing conditions, such as deposition times for layers 1002, 1003 and the amount of solder 1004 used per area of region 1003. Additionally, heating conditions used to flow the solder can also be changed based on the spatial properties to achieve adequate flow and or prevent migration of the solder.

Flat Panel Displays

The interferometry systems and methods disclosed herein can be used in the manufacture of flat panel displays such as, for example, liquid crystal displays (LCDs).

Figure 17A:
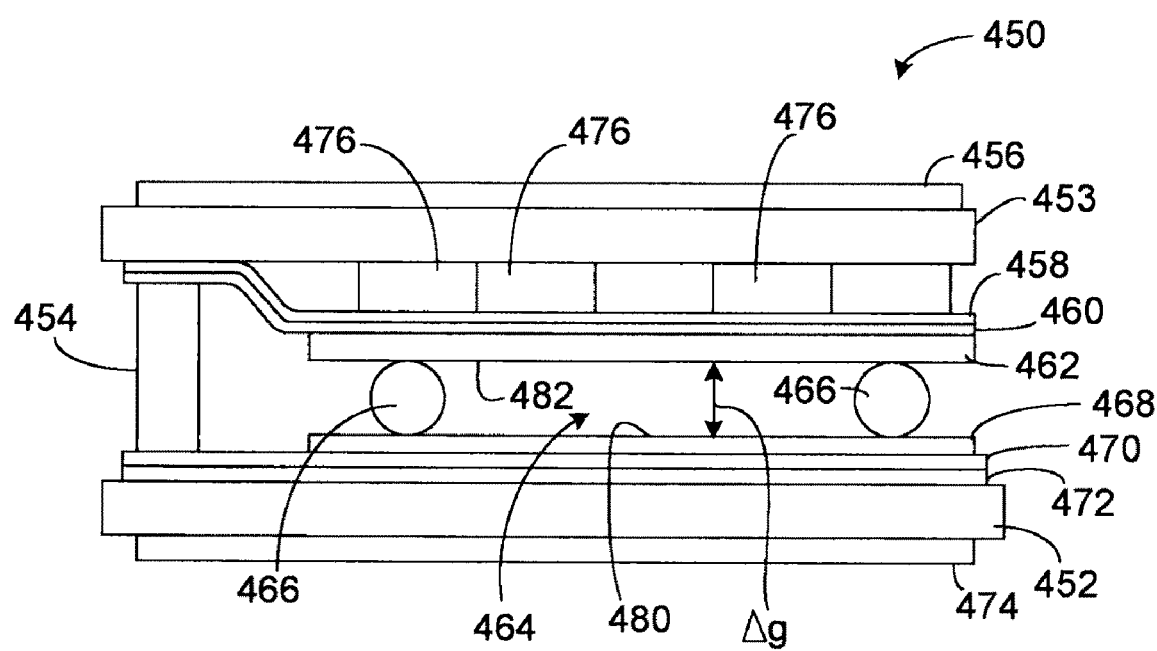
FIG. 17A is a schematic diagram of an LCD panel composed of several layers.

In general, a variety of different types of LCDs are used in many different applications, such as LCD televisions, desktop computer monitors, notebook computers, cell phones, automobile GPS navigation systems, automobile and aircraft entertainment systems to name a few. While the specific structure of LCDs can vary, many types of LCD utilize a similar panel structure. Referring to FIG. 17A, for example, in some embodiments, a LCD panel 450 is composed of several layers including two glass plates 452, 453 connected by an edge seal 454. Glass plates 452 and 453 are separated by a gap 464, which is filled with a liquid crystal material. Polarizers 456 and 474 are applied to the outer surfaces of glass plates 453 and 452, respectively. When integrated into a LCD, one of the polarizers operates to polarize light from the display's light source (e.g., a backlight, not shown) and the other polarizer serves as an analyzer, transmitting only that component of the light polarized parallel to the polarizer's transmission axis.

An array of color filters 476 is formed on glass plate 453 and a patterned electrode layer 458 is formed on color filters 476 from a transparent conductor, commonly Indium Tin Oxide (ITO). A passivation layer 460, sometimes called hard coat layer, commonly based on SiOx is coated over the electrode layer 458 to electrically insulate the surface. An alignment layer 462 (e.g., a polyimide layer) is disposed over the passivation layer 460 to align the liquid crystal material in gap 464.

Panel 450 also includes a second electrode layer 472 formed on glass plate 452. Another hard coat layer 470 is formed on electrode layer 472 and another alignment layer 468 is disposed on hard coat layer 470. In active matrix LCDs (AM LCDs), one of the electrode layers generally includes an array of thin film transistors (TFTs) (e.g., one or more for each sub-pixel) or other integrated circuit structures. A 3D surface profile of a TFT is shown in FIG. 12, for example.

The liquid crystal material is birefringent and modifies the polarization direction of light propagating through the LCD panel. The liquid crystal material also has a dielectric anisotropy and is therefore sensitive to electric fields applied across gap 464. Accordingly, the liquid crystal molecules change orientation when an electric field is applied, thereby varying the optical properties of the panel. By harnessing the birefringence and dielectric anisotropy of the liquid crystal material, one can control the amount of light transmitted by the panel.

The cell gap $\Delta g$, i.e., thickness of the liquid crystal material, is determined by spacers 466, which keep the two glass plates 452,453 at a fixed distance. In general, spacers can be in the form of preformed cylindrical or spherical particles having a diameter equal to the desired cell gap or can be formed on the substrate using patterning techniques (e.g., conventional photolithography techniques). The cell gap affects both the amount of optical retardation of light traversing the panel and the viscoelastic response of molecular alignment of the liquid crystal material, and therefore an important parameter to accurately control in LCD panel manufacturing.

In general, LCD panel manufacturing involves multiple process steps in forming the various layers. For example, referring to FIG. 17B, a process 499 includes forming the various layers on each glass plate in parallel, and then bonding the plates to form a cell. As illustrated, initially, TFT electrodes are formed (step 499A1) on a first glass plate. A passivation layer is formed (step 499A2) over the TFT electrodes, and then an alignment layer is formed (step 499A3) over the passivation layer. Next, spacers are deposited (step 499A4) on the alignment layer. Processing of the second glass plate typically involves forming color filters (step 499B1) and forming a passivation layer over the color filters (step 499C1). Then, electrodes (e.g., common electrodes) are formed (step 499B3) on the passivation layer, and an alignment layer is then formed (step 499B4) on the electrodes.

The cell is then formed by bonding the first and second glass plates together (step 499C1), and the cell is then filled with the liquid crystal material and sealed (step 499C2). After sealing, the polarizers are applied to the outer surface of each of the glass plates (step 499C3), providing the completed LCD panel. The combination and ordering of the steps shown in the flow chart are illustrative and, in general, other step combinations and their relative ordering can vary.

Figure 17B:
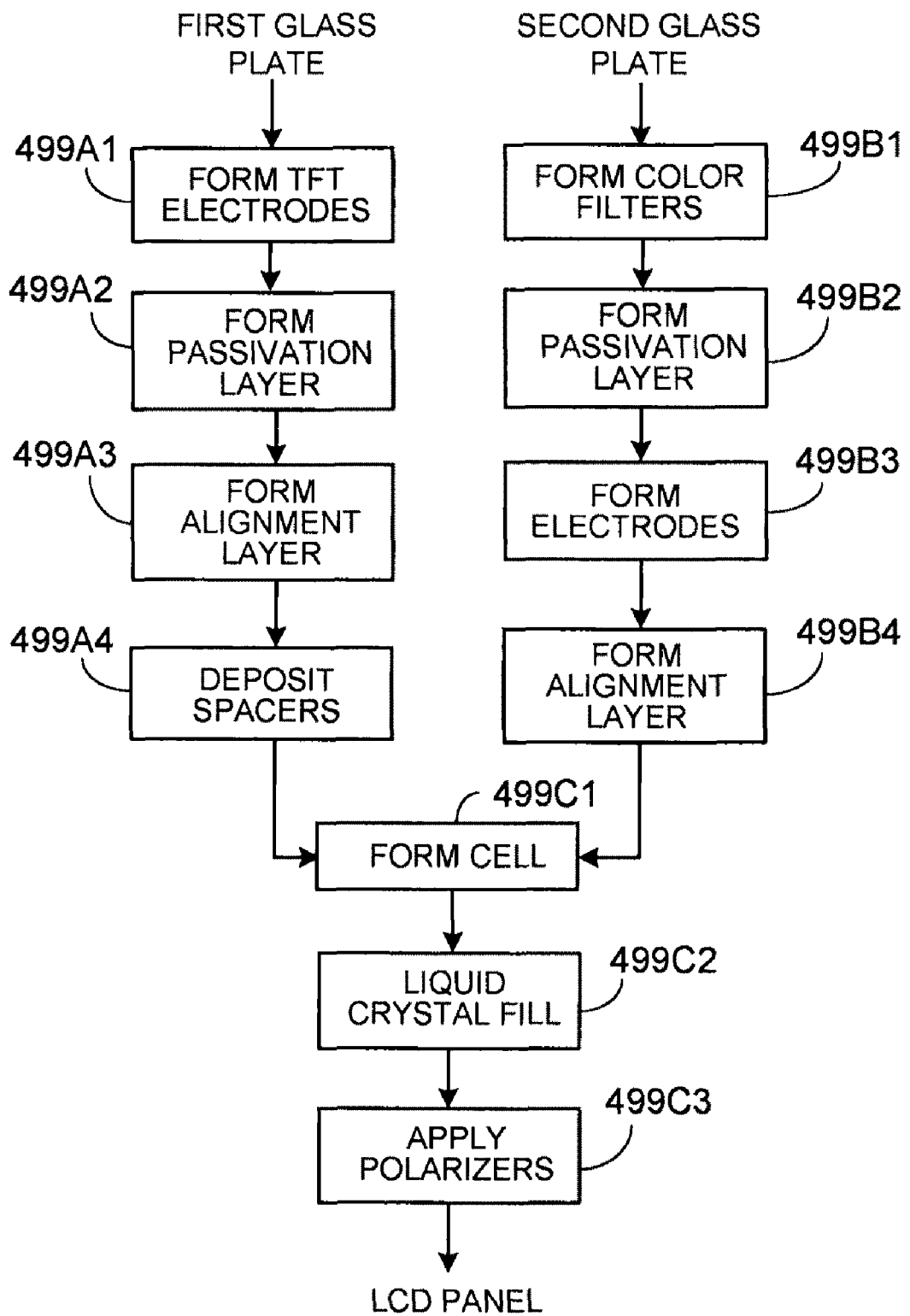
FIG. 17B is a flow chart showing various steps in LCD panel production.

Furthermore, each step illustrated in the flow chart in FIG. 17B can include multiple process steps. For example, forming the TFT electrodes (commonly referred to as "pixel electrodes") on the first glass plate involves many different process steps. Similarly, forming the color filters on the second glass plate can involve numerous process steps. Typically, forming pixel electrodes, for example, includes multiple process steps to form the TFTs, ITO electrodes, and various bus lines to the TFTs. In fact, forming the TFT electrode layer is, in essence, forming a large integrated circuit and involves many of the same deposition and photolithographic patterning processing steps used in conventional integrated circuit manufacturing. For example, various parts of the TFT electrode layer are built by first depositing a layer of material (e.g., a semiconductor, conductor, or dielectric), forming a layer of photoresist over the layer of material, and exposing the photoresist to patterned radiation. The photoresist layer is then developed, which results in a patterned layer of the photoresist. Next, portions of the layer of material lying beneath the patterned photoresist layer are removed in a etching process, thereby transferring the pattern in the photoresist to the layer of material. Finally, the residual photoresist is stripped from the substrate, leaving behind the patterned layer of material. These process steps can be repeated many times to lay down the different components of the TFT electrode layer, and similar deposition and patterning steps are often used to form color filters as well.

In general, the interferometry techniques disclosed herein can be used to monitor production of LCD panels at a variety of different stages of their production. For example, the interferometry techniques can be used to monitor the thickness and/or uniformity of photoresist layers used during LCD panel production. As explained previously, photoresist layers are used in lithographic patterning of TFT components and color filters, for example. For certain process steps, a layer of photoresist can be studied using a low coherence interferometry system prior to exposing the photoresist to patterned radiation. The low coherence interferometry systems can measure a thickness profile of the photoresist layer at one or more locations of the glass plate. Alternatively, or additionally, the techniques can be used to determine a surface profile of the photoresist layer. In either case, where the measured photoresist layer characteristics is within specified tolerance windows, the photoresist layer can be exposed to the desired patterned radiation. Where the photoresist layer is not within the specified window, it can be stripped from the glass plate and a new photoresist layer deposited.

In some embodiments, the interferometry techniques are used to monitor characteristics of a patterned photoresist layer. For example, critical dimensions (e.g., line widths) of patterned features can be studied. Alternatively, or additionally, the interferometry techniques can be used to determine overlay error between the features in the patterned resist and features beneath the photoresist layer. Again, where measured critical dimensions and/or overlay error are outside process windows, the patterned photoresist can be stripped from the substrate and a new patterned photoresist layer formed.

In certain embodiments, the interferometry techniques can be used in conjunction with half-tone photolithography. Increasingly, half-tone photolithography is used where specific thickness variations in the features of a patterned resist layer are desired. The low coherence interferometry techniques disclosed herein can be used to monitor thickness profiles of photoresist patterns in half-tone regions. In addition, the techniques can be used to determine both overlay and critical dimensions of these features.

In some embodiments, the interferometry techniques can be used to detect contaminants (e.g., foreign particles) at different stages on the glass plates at different stages of the production process. Such contaminants can give rise to visual defects (i.e., mura defects) in display panels, ultimately affecting the manufacturer's yield. Often, such defects are only detected by visual inspection, usually performed after the panel has been assembled. The interferometry techniques disclosed herein can be used to perform automated inspection of the glass plates at one or more points during the production process. Where particles are detected, the contaminated surface of the glass plate can be cleaned before the next production step. Accordingly, use of the techniques can reduce the occurrence of mura defects in panels, improving panel quality and reducing manufacturing costs.

Among other factors, the electrooptic properties (e.g., the contrast ratio and brightness) are dependent on the cell gap $\Delta g$. Cell gap control during manufacturing is often critical to obtaining uniform, quality displays. In certain embodiments, the disclosed interferometry techniques can be used to ensure that cell gap has desired uniformity. For example, the techniques can be used to monitor the height and/or position of spacers on a glass plate. Monitoring and controlling spacer height, for example, can reduce cell gap variations across a display.

In some cases, the actual cell gap may differ from the dimensions of spacers because, during assembly, pressure or vacuum is applied to introduce the liquid crystal medium, the edge seals cure and may change dimensions, and the added liquid crystal material can generates capillary forces between the glass plates. Both before and after adding the liquid crystal matter, the surfaces of the exposed layers on the glass plates reflect light that results in an interference pattern indicative of the cell gap $\Delta g$. The low coherence nature of the interference signal either itself or in combination with the described interference signal processing techniques can be used to monitor properties of the cell including the cell gap $\Delta g$ during manufacture even in the presence of interfaces formed by other layers of the cell.

An exemplary method can include obtaining a low coherence interference signal including interference patterns indicative of the cell gap $\Delta g$ prior to adding the liquid crystal material. The cell gap (or other spatial property of the cell) is determined from the interference patterns and can be compared to a specified value. Manufacturing conditions, e.g., a pressure or vacuum applied to the glass plates can be changed to modify the cell gap $\Delta g$ if a difference between the specified value and the determined cell gap exceeds tolerances. This process can be repeated until achieving the desired cell gap. Liquid crystal material is then introduced into the cell. The amount of liquid crystal medium to be added can be determined from the measured spatial property of the cell. This can avoid over- or underfilling the cell. The filling process can also be monitored by observing interference signals from the surfaces of the exposed layers on the glass plates. Once the cell has been filed, additional low coherence interference patterns are obtained to monitor the cell gap $\Delta g$ (or other spatial property). Again, the manufacturing conditions can be changed so that the cell gap is maintained or brought within tolerances.

In certain LCDs, the alignment layers include protruding structures that provide desired alignment characteristics to the liquid crystal material. For example, some LCDs have more than one alignment domain for each pixel of the display where protruding alignment structures provide the different align domains. Low coherence interferometry can be used to measure various properties of the protrusions, such as, for example, their shape, line width, height, and/or overlay error with respect to underlying features of the LCD panel. Where the protrusions are determined to be unsatisfactory, they can be repaired or removed and rebuilt as necessary.

In general, low coherence interferometry systems can be set up to monitor various stages of LCD panel production as desired. In some embodiments, inspection stations including an interferometry system can be set up in the manufacturing line itself. For example, monitoring stations can be installed in the clean manufacturing environment where the photolithography steps are performed. Delivery of the glass plates to and from the inspection stations can be entirely automated, being performed robotically. Alternatively, or additionally, inspection stations can be established removed from the manufacturing line. For example, where only a sampling of the displays are to be tested, the samples can be retrieved from the manufacturing line and taken offline for testing.

Figure 17C:
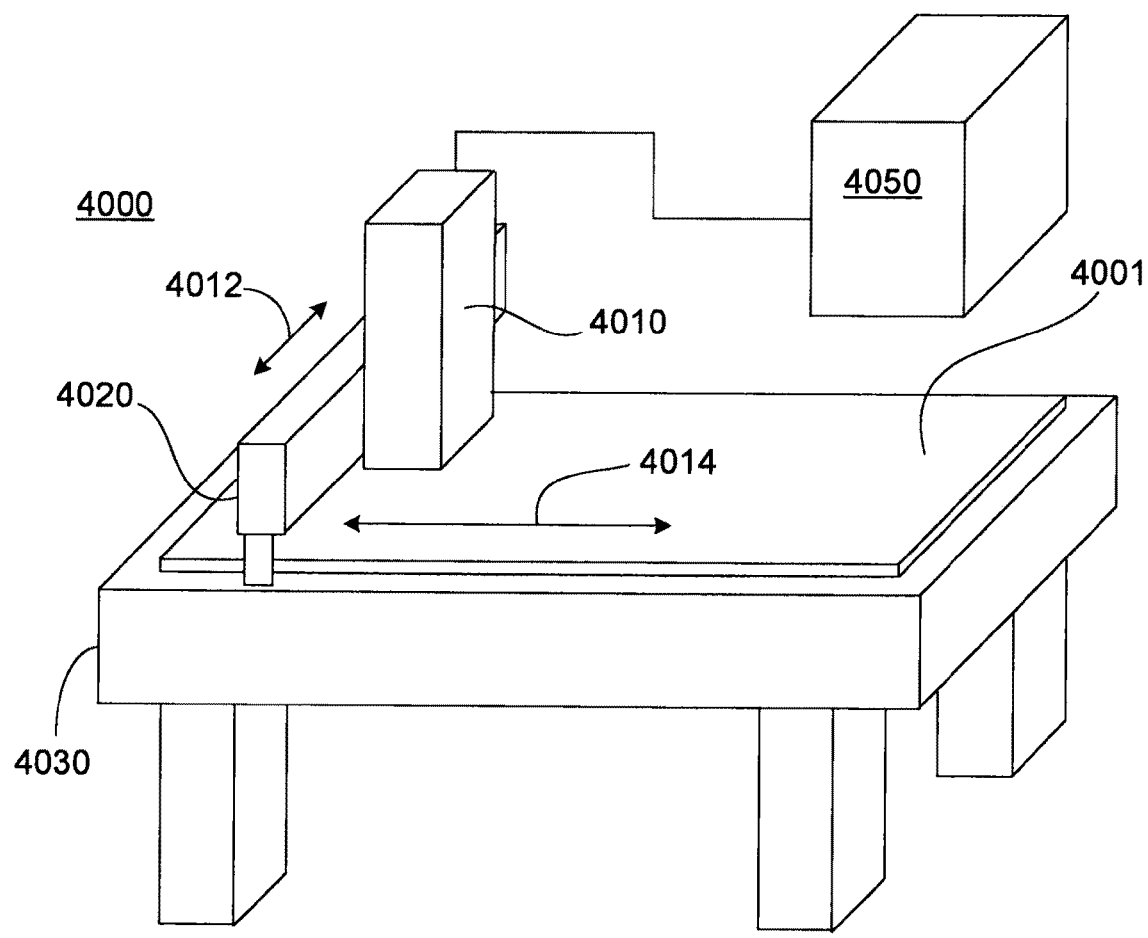
FIG. 17C is a diagram of an embodiment inspection station for LCD panels including an interferometric sensor.

Referring to FIG. 17C, an exemplary inspection station 4000 includes a table 4030, which includes a gantry 4020 on which an interferometric sensor 4010 (e.g., an interferometric microscope, such as disclosed previously) is mounted. Table 4030 (which can include vibration isolation bearings) supports a LCD panel 4001 (or glass plate) and positions panel 4001 with respect to sensor 4010. Sensor 4010 is mounted to gantry 4020 via a rail that allows the sensor to move back and forth in the direction of arrow 4012. Gantry 4020 is mounted on table 4030 on rails that allows the gantry to move back and forth in the direction of arrow 4014. In this way, inspection station 4000 can move sensor 4010 to inspect any location on display panel 4001.

Station 4000 also includes control electronics 4050 which controls the positioning system for sensor 4010 and acquires the signals from sensor 4010 that include information about panel 4001. In this way, control electronics 4050 can coordinate sensor positioning with data acquisition.

Laser Scribing and Cutting

Lasers can be used to scribe objects in preparation for separating different, concurrently manufactured structures, e.g., microelectronics structures. The quality of separation is related to the scribing conditions, e.g., laser focus size, laser power, translation rate of the object, and scribe depth. Because the density of features of the structure may be large, the scribe lines may be adjacent thin film or layers of the structures. Interfaces associated with the thin film or layers may create interference patterns that appear when interferometry is used to determine the scribe depth. The methods and systems described herein can be used to determine the scribe depth even in the presence of such adjacent films or layers.

An exemplary method can include scribing one or more electronic structures and separating the structures along the scribe lines. Before and/or after separation, low coherence interference signals can be used to determine the depth of scribe. Other scribing conditions are known, e.g., laser spot size, laser power, translation rate. The scribe depth can be determined from the interference signals. The quality of separation as a function of the scribing conditions, including the scribe depth, can be determined by evaluating the separated structures. Based on such determinations, the scribing conditions necessary to achieve a desired separation quality can be determined. During continued manufacturing, low coherence interference signals can be obtained from scribed regions to monitor the process. Scribing conditions can be changed to maintain or bring the scribe properties within tolerances.

A number of embodiments of the invention have been described. Other embodiments are in the claims.

What is claimed is:

1. A computer-implemented method, comprising:
    comparing, using one or more computer-processors, a scanning interferometry signal obtained for a location of a test object to each of multiple model signals corresponding to different model parameters for modeling the test object;
    wherein for each model signal the comparing comprises calculating a correlation function between the scanning interferometry signal and the model signal to identify a surface-height offset between the scanning interferometry signal and the model signal and, based on the identified surface-height offset, calculating a height-offset compensated merit value indicative of a similarity between the scanning interferometry signal and the model signal for a common surface height,
    wherein calculating the height-offset compensated merit value comprises compensating a frequency domain representation of the scanning interferometry signal or a frequency domain representation of the model signal with a linear phase term having a slope corresponding to the identified surface-height offset and quantifying the similarity between the scanning interferometry signal and the model signal following the phase compensation; and
    based on the respective merit values for the different model signals, determining a test object parameter at the location of the test object.

2. The method of claim 1, wherein the calculated correlation function is based on a frequency domain representation of the scanning interferometry signal and a frequency domain representation of the model signal.

3. The method of claim 2, wherein calculating the correlation function comprises inverse transforming the product of the frequency domain representations of the scanning interferometry signal and the model signal into the scan coordinate domain.

4. The method of claim 1, wherein the identified surface-height offset corresponds to a peak in the calculated correlation function.

5. The method of claim 4, wherein the peak is determined by interpolating the correlation function between scan-positions.

6. The method of claim 1, wherein identifying the surface-height offset comprises determining a phase difference between the scanning interferometry signal and the model signal.

7. The method of claim 1, wherein determining the phase difference comprises determining a complex phase of the correlation function at a peak positioning the correlation function.

8. The method of claim 1, wherein the phase compensation is applied to the frequency domain representation of the scanning interferometry signal to produce a frequency domain representation of the scanning interferometry signal corresponding to a surface height common to that used for modeling the model signal.

9. The method of claim 1, wherein the quantification of the similarity between the scanning interferometry signal and the model signal following the phase compensation is performed in the frequency domain.

10. The method of claim 1, wherein the phase compensation of the frequency domain representation of the interferometry signal comprises multiplying a spectral component with a linear phase factor $\exp(-iK\zeta_{offset})$, where K is the fringe frequency component and $\zeta_{offset}$ is the identified surface-height offset.

11. The method of claim 1, wherein the phase compensation of the frequency domain representation of the interferometry signal comprises multiplying a spectral component with a phase factor $\exp(-iA_{peak})$, where $A_{peak}$ is the complex phase of the correlation function at a peak of the calculated correlation function.

12. The method of claim 1, wherein the phase compensation of the frequency domain representation of the interferometry signal comprises removing a linear portion of the phase change within the spectrum.

13. The method of claim 1, wherein the phase compensation comprises removing a phase difference between the interferometry spectrum and the model spectrum arising from the surface-height offset between the scanning interferometry signal and the model signal.

14. The method of claim 1, wherein calculating the height-offset compensated merit value is based on a frequency domain representation of the scanning interferometry signal and a frequency domain representation of the model signal.

15. The method of claim 1, wherein calculating the height-offset compensated merit value is restricted to a region of interest in the frequency domain.

16. The method of claim 1, wherein calculating the height-offset compensated merit value is based on a least-square difference between the phase-compensated interferometry spectrum and the model spectrum.

17. The method of claim 1, wherein calculating the height-offset compensated merit value is based on a complex phase of the correlation function at the peak position.

18. The method of claim 1, wherein calculating the height-offset compensated merit value is based on the peak value of the correlation function at the peak position.

19. The method of claim 1, wherein calculating the height-offset compensated merit value is based on normalizing the frequency domain representation of the scanning interferometry signal or the frequency domain representation of the model signal.

20. The method of claim 1, wherein the model parameters corresponding to the model signals comprise one or more parameters relating to an under-resolved surface feature.

21. The method of claim 1, wherein determining a test object parameter comprises determining more than one test object parameter based on the respective merit values.

22. The method of claim 1, wherein determining a test object parameter comprises identifying a matching model signal based on comparing the height-offset compensated merit values.

23. The method of claim 22, wherein determining the test object parameter is based on the matching model signal.

24. The method of claim 1, wherein determining the test object parameter comprises corrections based on a complex phase of the correlation function at the peak.

25. The method of claim 1, wherein comparing a scanning interferometry signal to each of multiple model signals and determining a test object parameter are repeated for each of multiple scanning interferometry signals corresponding to different surface locations of the test object.

26. The method of claim 1, wherein the interferometry signal is obtained by imaging test light emerging from the test object to interfere with reference light on a detector, and varying an optical path length difference from a common source to the detector between interfering portions of the test and reference light, wherein the test and reference light are derived from the common source, and wherein the interferometry signal corresponds to an interference intensity measured by the detector as the optical path length difference is varied.

27. The method of claim 26, wherein the common source has a spectral coherence length, and the optical path length difference is varied over a range larger than the spectral coherence length to produce the scanning interferometry signal.

28. A process for making a display panel, comprising:
providing a component of the display panel;
determining information about the component using the method of claim 1, wherein the component corresponds to the test object and the information is based on the test object parameter and
forming the display panel using the component.

29. An interferometer, comprising:
an optical system configured to obtain an scanning interferometry signal from a surface location of an object; and
a processor comprising code configured to:
i) receive multiple model signals corresponding to different model parameters for modeling the test object, compare the scanning interferometry signal to each of multiple model signals, wherein for each model signal the comparing comprises calculating a correlation function between the scanning interferometry signal and the model signal to identify a surface-height offset between the scanning interferometry signal and the model signal and, based on the identified surface-height offset, calculating a height-offset compensated merit value indicative of a similarity between the scanning interferometry signal and the model signal for an approximated common surface height,
wherein calculating the height-offset compensated merit value comprises compensating a frequency domain representation of the scanning interferometry signal or a frequency domain representation of the model signal with a linear phase term having a slope corresponding to the identified surface-height offset and quantifying the similarity between the scanning interferometry signal and the model signal following the phase compensation; and
ii) based on the respective merit values for the different model signals, determine a test object parameter at the location of the test object.

30. A computer-implemented method, comprising:
comparing, using one or more computer-processors, a scanning interferometry signal obtained for each of multiple locations of a test object to each of multiple model signals corresponding to different model parameters for modeling the test object;
wherein for each test object location and each model signal the comparing comprises calculating a correlation function between the scanning interferometry signal and the model signal based on a frequency domain representation of the scanning interferometry signal and a frequency domain representation of the model signal to identify a surface-height offset between the scanning interferometry signal and the model signal and, based on the identified surface-height offset, calculating a height-offset compensated merit value indicative of a similarity between the scanning interferometry signal and the model signal for a common surface height
wherein calculating the height-offset compensated merit value comprises compensating a frequency domain representation of the scanning interferometry signal or a frequency domain representation of the model signal with a linear phase term having a slope corresponding to the identified surface-height offset and quantifying the similarity between the scanning interferometry signal and the model signal following the phase compensation; and
based on the respective merit values for the different model signals at each of the different test object locations, determining one or more test object parameters at each test object location.

31. The computer-implemented method of claim 30, further comprising obtaining the scanning interferometry signal with a detector, wherein obtaining the scanning interferometry signal includes imaging test light emerging from the test object to interfere with reference light on the detector.

32. A computer-implemented method, comprising:
for at least one model signal of a set of model signals, calculating, using one or more computer-processors, a height-offset compensated merit value indicative of a similarity between a scanning interferometry signal and the model signal for a common surface height,
wherein calculating the height-offset compensated merit value comprises:
performing a correlation of the scanning interferometry signal or information derived thereof and the model signal or information derived thereof;
based on the correlation, determining a height-dependent phase slope between a frequency domain representation of the interferometry signal and a frequency domain representations of the model signal and compensating the phases of the coefficients of at least one of the frequency domain representations of the interferometry signal and the model signal; and
based on the height-offset compensated merit value, determining a test object parameter.

33. The computer-implemented method of claim 32, further comprising obtaining the scanning interferometry signal with a detector, wherein obtaining the scanning interferometry signal includes imaging test light emerging from a test object to interfere with reference light on the detector.

* * * * *

UNITED STATES PATENT AND TRADEMARK OFFICE
CERTIFICATE OF CORRECTION

| | | |
|---|---|---|
| PATENT NO. | : 8,126,677 B2 | Page 1 of 1 |
| APPLICATION NO. | : 12/332674 | |
| DATED | : February 28, 2012 | |
| INVENTOR(S) | : Peter De Groot and Xavier Colonna De Lega | |

It is certified that error appears in the above-identified patent and that said Letters Patent is hereby corrected as shown below:

Page 32, Claim 30, Line 23, after "height" insert --,--.

Signed and Sealed this
Twentieth Day of November, 2012

David J. Kappos
*Director of the United States Patent and Trademark Office*